(12) United States Patent
Imoto et al.

(10) Patent No.: US 10,421,055 B2
(45) Date of Patent: *Sep. 24, 2019

(54) DISPERSION AND METHOD FOR FORMING HYDROGEL

(71) Applicant: NISSAN CHEMICAL INDUSTRIES, LTD., Tokyo (JP)

(72) Inventors: Takayuki Imoto, Funabashi (JP); Takehisa Iwama, Funabashi (JP)

(73) Assignee: NISSAN CHEMICAL INDUSTRIES, LTD., Tokyo (JP)

(*) Notice: Subject to any disclaimer, the term of this patent is extended or adjusted under 35 U.S.C. 154(b) by 394 days.

This patent is subject to a terminal disclaimer.

(21) Appl. No.: 14/410,330

(22) PCT Filed: Jun. 25, 2013

(86) PCT No.: PCT/JP2013/067407
§ 371 (c)(1),
(2) Date: Dec. 22, 2014

(87) PCT Pub. No.: WO2014/003015
PCT Pub. Date: Jan. 3, 2014

(65) Prior Publication Data
US 2015/0202586 A1    Jul. 23, 2015

(30) Foreign Application Priority Data
Jun. 25, 2012 (JP) .................................. 2012-141932

(51) Int. Cl.
| | | |
|---|---|---|
| *B01J 13/00* | (2006.01) | |
| *A61K 8/64* | (2006.01) | |
| *A61K 9/00* | (2006.01) | |
| *A61K 8/33* | (2006.01) | |
| *A61K 8/34* | (2006.01) | |
| *A61Q 19/00* | (2006.01) | |
| *A61K 8/04* | (2006.01) | |
| *A61K 47/42* | (2017.01) | |
| *A61K 9/06* | (2006.01) | |

(52) U.S. Cl.
CPC .............. *B01J 13/0065* (2013.01); *A61K 8/04* (2013.01); *A61K 8/042* (2013.01); *A61K 8/33* (2013.01); *A61K 8/34* (2013.01); *A61K 8/345* (2013.01); *A61K 8/64* (2013.01); *A61K 9/0009* (2013.01); *A61Q 19/00* (2013.01); *A61K 9/06* (2013.01); *A61K 47/42* (2013.01); *A61K 2800/48* (2013.01)

(58) Field of Classification Search
CPC ..... B01J 13/0065; B01J 35/0065; A61K 8/04; A61K 8/33; A61K 8/34; A61K 2800/48; C07K 5/00; C07K 5/04–1027
See application file for complete search history.

(56) References Cited

U.S. PATENT DOCUMENTS

| | | | | |
|---|---|---|---|---|
| 8,999,300 | B2* | 4/2015 | Iwama ............... | A61K 8/64 424/195.18 |
| 9,265,833 | B2* | 2/2016 | Miyamoto ........... | A61K 9/0014 |
| 9,333,158 | B2* | 5/2016 | Miyamoto ............ | A61K 8/046 |
| 9,480,772 | B2* | 11/2016 | Goto ................... | A61K 9/0014 |
| 9,782,331 | B2* | 10/2017 | Imoto ................ | C07K 5/06026 |
| 10,105,294 | B2* | 10/2018 | Imoto ................ | C07K 5/06026 |
| 2011/0183913 | A1* | 7/2011 | Miyamoto ........... | A61K 9/0014 514/18.8 |
| 2012/0035108 | A1* | 2/2012 | Miyamoto ............ | A61K 8/046 514/9.1 |
| 2012/0258059 | A1* | 10/2012 | Iwama ................ | A61K 8/64 424/59 |
| 2013/0296761 | A1* | 11/2013 | Goto ................... | A61K 9/0014 602/54 |
| 2016/0129119 | A1* | 5/2016 | Imoto ................ | C07K 5/06026 514/773 |
| 2017/0209522 | A1* | 7/2017 | Haga ................. | A61K 38/05 |

(Continued)

FOREIGN PATENT DOCUMENTS

| | | | |
|---|---|---|---|
| JP | 2011-036760 A | | 2/2011 |
| JP | 2011057620 A | * | 3/2011 |

(Continued)

OTHER PUBLICATIONS

Machine Translation of Publ. No. JP 2012-186056 A, published Sep. 2012, Japan Patent Office, Tokyo, Japan, online at https://dossier1.j-platpat.inpit.go.jp/tri/all/odse/ODSE_GM101_Top.action (Downloaded Jan. 7, 2017), pp. 1-20.*

Machine Translation of Publ. No. JP 2011-057620 A, published Mar. 2011, Japan Patent Office, Tokyo, Japan, online at https://dossier1.j-platpat.inpit.go.jp/tri/all/odse/ODSE_GM101_Top.action (Downloaded Jan. 7, 2017), pp. 1-28.*

Suzuki et al., "Supramolecular Hydrogels Formed by L-Lysine Derivatives", Chemistry Letters, Nov. 5, 2004, pp. 1496-1497, vol. 33, No. 11.

Jung et al., "Self-Assembly of a Sugar-Based Gelator in Water: Its Remarkable Diversity in Gelation Ability and Aggregate Structure", Langmuir, Nov. 13, 2001, pp. 7229-7232, vol. 17, No. 23.

(Continued)

*Primary Examiner* — Stephen E Rieth
(74) *Attorney, Agent, or Firm* — Oliff PLC

(57) ABSTRACT

There is provided a dispersion containing a lipid peptide type compound useful as a low molecular weight gelator and a solvent capable of dissolving the lipid peptide type compound at a lower temperature. There is provided also a dispersion from which a hydrogel can be formed by a simpler method and from which a gel can be obtained as a gel having high thermal stability, and provide a method for forming the gel. A dispersion including a lipid peptide type compound in which a peptide portion having an amino acid repeating bonding structure is bonded to a lipid portion consisting of a $C_{9-23}$ aliphatic group; and at least one alcohol selected from the group consisting of 1,2-alkanediol, 1,3-alkanediol, and ethylene glycol monoalkyl ether or a mixed solution of the at least one alcohol and water; and a method for producing a hydrogel by use of the dispersion.

17 Claims, No Drawings

(56) References Cited

U.S. PATENT DOCUMENTS

2018/0000716 A1* 1/2018 Goto ............... A61K 8/64
2018/0021250 A1* 1/2018 Goto ............... A61K 9/0014

FOREIGN PATENT DOCUMENTS

| | | | |
|---|---|---|---|
| JP | 2011-240215 A | | 12/2011 |
| JP | 2012-030221 A | | 2/2012 |
| JP | 2012186056 A | * | 9/2012 |
| WO | 2009005151 A1 | | 1/2009 |
| WO | 2009005152 A1 | | 1/2009 |
| WO | WO 2010/013555 A1 | * | 2/2010 |
| WO | 2010106981 A1 | | 9/2010 |
| WO | 2011052613 A1 | | 5/2011 |
| WO | WO 2012/063947 A1 | * | 5/2012 |

OTHER PUBLICATIONS

Hamachi et al., "Solid-phase Lipid Synthesis (SPLS)-2: Incidental Discovery of Organogelators Based on Artificial Glycolipids", Tetrahedron Letters, 2001, pp. 6141-6145, vol. 42.

Hamachi et al., "Solid Phase Lipid Synthesis (SPLS) for Construction of an Artificial Glycolipid Library", Chemical Communications The Royal Society of Chemistry, Jun. 26, 2000, pp. 1281-1282.

Suzuki et al., "Supramolecular Hydrogel Formed by Glucoheptonamide of L-lysine: Simple Preparation and Excellent Hydrogelation Ability", Feb. 20, 2007, Tetrahedron, pp. 7302-7308, vol. 63.

Matsuzawa et al., "Assembly and Photoinduced Organization of Mono- and Oligopeptide Molecules Containing an Azobenzene Moiety", Advanced Functional Materials, Jun. 18, 2007, pp. 1507-1514, vol. 17, No. 9.

Oct. 1, 2013 Search Report issued in International Patent Application No. PCT/JP2013/067407.

Oct. 1, 2013 Written Opinion of the International Patent Application No. PCT/JP2013/067407.

* cited by examiner

DISPERSION AND METHOD FOR FORMING HYDROGEL

TECHNICAL FIELD

The present invention relates to a dispersion containing a low molecular weight lipid peptide type compound useful as a thickener or a gelator, and a method for forming a hydrogel using the dispersion.

BACKGROUND ART

A hydrogel contains water as the solvent and thus is useful as a gel having high biocompatibility. Such a hydrogel is used in various fields such as applications for commodities such as paper diapers, cosmetics and aromatics.

Examples of a conventional hydrogel include polymer gels formed through such steps that polymer chains are cross-linked to form a three-dimensional network structure, and that a noncovalent bond is formed between the three-dimensional network structure and the solvent such as water, so that the three-dimensional network structure swells to form a polymer gel. Many studies for the physical properties of the polymer gel and many developments of the applications of the polymer gel have been performed with respect to natural polymer gels formed from polysaccharide such as agarose and protein, and synthetic polymer gels in which polymer chains are cross-linked to each other through a chemical covalent bond, such as an acrylamide gel.

Recently, besides the above gels containing polymer compounds, hydrogels formed by the self-assembly of an organic compound having a relatively low molecular weight have been found and various hydrogels have been studied.

The formation of the gel by the self-assembly of a low molecular weight compound has been elucidated to occur through the following steps: in a substances (low molecular weight compounds) group in a random state at first, molecules of the substances group associate spontaneously while they are having directionality by, for example, an intermolecular non-covalent interaction between the molecules of the substances under an appropriate external condition (in a medium) to form a macro molecule-assembly: and plural macro molecule-assemblies form a network and the network swells with a surrounding solvent to form a gel. Examples of a driving force for this molecule association (self-assembly) include a force by an action of a hydrogen bond having a relatively weak bonding strength, and a force by a van der Waals interaction (non-hydrogen bond) having a bonding strength further weaker than that of the hydrogen bond.

Many of the low molecular weight gelators that have been disclosed are an amphipathic compound having a combination of a hydrophobic portion of a long-chain alkyl group and a hydrophilic portion. Examples thereof include an amphipathic compound in which the hydrophilic portion is an amino acid [Non-patent Document 1], an amphipathic compound in which the hydrophilic portion is a peptide [Patent Documents 1 and 2], an amphipathic compound in which the hydrophilic portion is a monosaccharide or a polysaccharide [Non-patent Documents 2 and 3], and an amphipathic compound in which the hydrophilic portion is a polyol [Non-patent Document 4]. In addition, there has also been disclosed a low molecular weight gelator utilizing such a tendency that a peptide made up with valine takes easily a β-sheet structure [Non-patent Document 5].

Such a low molecular weight hydrogelator can form a hydrogel by a method including: heating and stirring the hydrogelator and water as the solvent under a temperature condition of about 100° C. to dissolve and disperse the gelator in water; and leaving the resultant solution to stand still at room temperature.

PRIOR ART DOCUMENTS

Patent Documents

Patent Document 1: International Publication No. WO 2009/005151 pamphlet
Patent Document 2: International Publication No. WO 2009/005152 pamphlet

Non-Patent Documents

Non-patent Document 1: Suzuki, Masahiro. Yumoto, Mariko. Mutsumi, Shirai. Hirofusa, Hanabusa, Kenji. Chemistry Letters, 33(11), 1496-1497.
Non-patent Document 2: Jong Hwa Jung, Georeg John, Mitsutosish Mausda, Kaname Yoshida, Seiji Shinnkai, and Toshimi Shimizu Langumir 2001, 17, 7229-7232
Non-patent Document 3: I. Hamachi, S. Kiyonaka, S. Shinkai, Tetrahedron Lett., 2001, 42, 6141. I. Hamachi, S. Kiyonaka, S. Shinaki, Chem. Commun., 2000, 1281
Non-patent Document 4: Masahiro Suzuki, Sanae Owa, Hirofusa Shirai and Kenji Hanabusa, Tetrahedron 2007 63 7302-7308
Non-patent Document 5: Yoko Matsuzawa, Katsuyuki Ueki, Masaru Yoshida, Nobuyuki Tamaoki, Tohru Nakamura, Hideki Sakai, and Masahiko Abe, Adv. Funct. Mater. 2007, 17, 1507-1514

SUMMARY OF THE INVENTION

Problem to be Solved by the Invention

It is an object of the present invention to provide a dispersion containing a lipid peptide type compound useful as a low molecular weight gelator, such as a lipid dipeptide and a lipid tripeptide, and a solvent capable of dissolving the lipid peptide type compound at a lower temperature more easily.

It is also an object of the present invention to provide a dispersion from which a hydrogel can be formed by a simpler method and under a milder condition (low temperature) and from which a gel can be obtained as a gel having high thermal stability, and provide a method for forming the gel.

Means for Solving the Problems

As a result of assiduous research intended to overcome these disadvantages, the inventors of the present invention have found that a lipid peptide type compound containing a low molecular weight lipid peptide or a pharmaceutically acceptable salt thereof exhibits high solubility and high dispersibility relative to a specific solvent having, in the molecule thereof, a hydrophilic portion and a hydrophobic portion under a condition of a temperature lower than a temperature in the case of a conventional lipid peptide type compound, and becomes a dispersion suitable as a premix raw material for a gel or a thickener for an antifreezing fluid.

The inventors of the present invention have also found that by adding a polymer emulsifier to the dispersion in which the lipid peptide type compound is dissolved in the solvent, upon preparing a gel using the dispersion, even when the gelator dispersion is subjected to stirring-cooling down, a gel can be satisfactorily formed, and that the dispersion is useful as a premix for a gel applicable to cosmetics or quasi-drugs. The inventors of the present invention have further found that by adding a heat resistance improver to the dispersion, high thermal stability can be imparted to the gel obtained using the dispersion, and have completed the present invention.

Specifically, the present invention relates to, according to a first aspect, a dispersion comprising:

a lipid peptide type compound in which a peptide portion having an amino acid repeating bonding structure is bonded to a lipid portion consisting of a $C_{9-23}$ aliphatic group; and at least one alcohol selected from the group consisting of 1,2-alkanediol, 1,3-alkanediol, and ethylene glycol mono-alkyl ether or a mixed solution of the at least one alcohol and water.

The present invention relates to, according to a second aspect, the dispersion according to the first aspect, characterized in that the lipid peptide type compound contains at least one of compounds of Formula (1) to Formula (3) and pharmaceutically acceptable salts of the compounds:

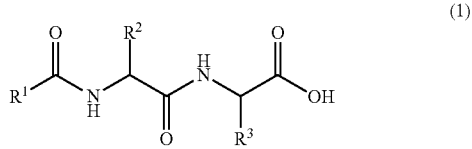

(1)

(where $R^1$ is a $C_{9-23}$ aliphatic group; $R^2$ is a hydrogen atom or a $C_{1-4}$ alkyl group optionally having a $C_{1-2}$ branching chain; $R^3$ is a —$(CH_2)_n$—X group; n is a number of 1 to 4; and X is an amino group, a guanidino group, a —$CONH_2$ group, or a 5-membered ring optionally having 1 to 3 nitrogen atom(s), a 6-membered ring optionally having 1 to 3 nitrogen atom(s), or a fused heterocyclic ring composed of a 5-membered ring and a 6-membered ring which optionally have 1 to 3 nitrogen atom(s)),

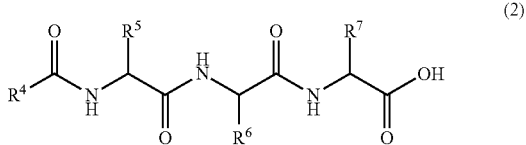

(2)

(where $R^4$ is a $C_{9-23}$ aliphatic group; $R^5$ to $R^7$ are each independently a hydrogen atom, a $C_{1-4}$ alkyl group optionally having a $C_{1-2}$ branching chain, or a —$(CH_2)_n$—X group; n is a number of 1 to 4; X is an amino group, a guanidino group, a —$CONH_2$ group, or a 5-membered ring optionally having 1 to 3 nitrogen atom(s), a 6-membered ring optionally having 1 to 3 nitrogen atom(s), or a fused heterocyclic ring composed of a 5-membered ring and a 6-membered ring which optionally have 1 to 3 nitrogen atom(s)), and

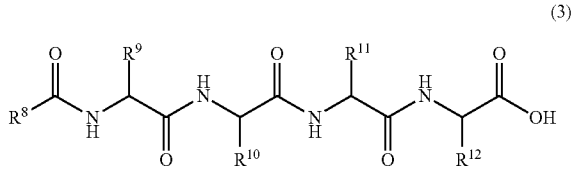

(3)

(where $R^8$ is a $C_{9-23}$ aliphatic group; $R^9$ to $R^{12}$ are each independently a hydrogen atom, a $C_{1-4}$ alkyl group optionally having a $C_{1-2}$ branching chain, or a —$(CH_2)_n$—X group; n is a number of 1 to 4; X is an amino group, a guanidino group, a —$CONH_2$ group, or a 5-membered ring optionally having 1 to 3 nitrogen atom(s), a 6-membered ring optionally having 1 to 3 nitrogen atom(s), or a fused heterocyclic ring composed of a 5-membered ring and a 6-membered ring which optionally have 1 to 3 nitrogen atom(s)).

The present invention relates to, according to a third aspect, the dispersion according to the first aspect or the second aspect, further comprising a polymer emulsifier, in which the lipid peptide type compound serves as a gelator.

The present invention relates to, according to a fourth aspect, the dispersion according to the third aspect, in which the dispersion is a premix for preparing a cosmetic or a quasi-drug.

The present invention relates to, according to a fifth aspect, the dispersion according to the first aspect or the second aspect, in which the dispersion is used as a thickener for an antifreezing fluid.

The present invention relates to, according to a sixth aspect, the dispersion according to the third aspect or the fourth aspect, in which the polymer emulsifier is at least one polymer compound selected from the group consisting of a graft polymer compound in which a hydrophobic moiety is grafted to a hydrophilic backbone and a block polymer compound containing a hydrophobic structural unit and a hydrophilic structural unit.

The present invention relates to, according to a seventh aspect, the dispersion according to the sixth aspect, further comprising a heat resistance improver.

The present invention relates to, according to an eighth aspect, the dispersion according to the seventh aspect, in which the heat resistance improver is at least one fatty acid selected from the group consisting of a saturated $C_{10-20}$ fatty acid, an unsaturated $C_{10-20}$ fatty acid, and a salt of these fatty acids.

The present invention relates to, according to a ninth aspect, the dispersion according to the eighth aspect, in which the heat resistance improver is capric acid, lauric acid, myristic acid, palmitic acid, or stearic acid.

The present invention relates to, according to a tenth aspect, the dispersion according to any one of the sixth aspect to the ninth aspect, in which the polymer compound is selected from the group consisting of a carboxymethyl cellulose and an alginic acid ester.

The present invention relates to, according to an eleventh aspect, the dispersion according to the tenth aspect, in which the polymer compound is propylene glycol alginate.

The present invention relates to, according to a twelfth aspect, a method for producing a hydrogel, the method comprising:

adding the dispersion as described in any one of the third aspect, the fourth aspect, and the sixth aspect to the eleventh aspect to water and heating the resultant mixture to a temperature that is room temperature or higher and lower than 100° C.; and cooling down the mixture with stirring until the temperature of the mixture reaches a temperature lower than the temperature in the heating and forming a gel.

The present invention relates to, according to a thirteenth aspect, a hydrogel formed using the dispersion as described in any one of the third aspect, the fourth aspect, and the sixth aspect to the eleventh aspect.

Effects of the Invention

The dispersion of the present invention can be prepared by stirring the lipid peptide type compound and 1,2-alkanediol or the like under a relatively mild temperature condition such as at 80° C. to dissolve and disperse the lipid peptide type compound within a relatively short time. The dispersion of the present invention is a dispersion suitable as a premix raw material for a gel or a thickener for an antifreezing fluid.

A polymer emulsifier is added to the dispersion of the present invention. This can provide a satisfactory hydrogel without forming insoluble matters or deposits in the preparation of a gel using the dispersion under a mild temperature condition such as at 80° C. and even while the dispersion is stirred and cooled down. The dispersion of the present invention is useful as a premix for a gel applicable to cosmetics or quasi-drugs.

Further, the dispersion of the present invention to which a heat resistance improver is added can impart high thermal stability to the gel formed using the dispersion.

The lipid peptide type compound contained in the dispersion of the present invention is an artificial low molecular weight compound composed only of a lipid and a peptide having extremely high safety and 1,2-alkanediol, 1,3-alkanediol, and ethylene glycol monoalkyl ether are an additive applicable to foods, cosmetics, and medicines. That is, the dispersion of the present invention has high biological safety and particularly, from the viewpoint of high safety required for a cell culture base material, medical materials, materials for cosmetics, or the like, the dispersion of the present invention is useful in the above applications.

Further, the dispersion of the present invention can form a gel by gelling water without using a cross-linking agent or the like required during the formation of, for example, a synthetic polymer type gel which has been conventionally disclosed. Thus, no unreacted substance such as an unreacted cross-linking agent remains in the obtained hydrogel. Moreover, the lipid peptide type compound contained in the dispersion can form a hydrogel only with a small adding amount of around 1% by mass, and applies low load to the environment and the organism when the lipid peptide type compound is incorporated into them.

The method for producing a hydrogel of the present invention can form a gel under a relatively mild condition such as at lower than 100° C. and even while the heated gelator dispersion is stirred. Even when an additive for cosmetics or an additive for quasi-drugs for which influences of heat on these additives are desired to be eliminated as much as possible, is added to the dispersion, the method for forming a hydrogel of the present invention can form a hydrogel without degenerating these additives.

The gel of the present invention can be obtained by adding a smaller amount of a gelator than that for a conventional gel as described above, so that it can be mentioned that the gel of the present invention is a gel having high safety both in the organism and in the environment.

Further, as described above, when a gel obtained from a lipid peptide which is a low molecular weight compound is used in an external environment, for example in the soil, the gel is easily degraded by soil bacteria or the like, or when the gel is used in an organism, the gel is easily degraded by metabolic enzyme, so that it applies low load to the environment and the organism.

The gel of the present invention is a gel that is capable of being formed under a relatively mild condition and to which additives that may be influenced by heat, can be blended.

MODES FOR CARRYING OUT THE INVENTION

Hereinafter, the present invention is described in detail together with the circumstances leading to the completion of the present invention.

A conventionally disclosed low molecular weight gelator, for example, a gelator containing as the hydrophilic portion, a peptide (a lipid peptide, in Patent Documents 1 and 2) exhibits low solubility in a solvent, so that for causing the gelator to gel a solvent, it is necessary that first, a solvent desired to be gelled is heated to a high temperature such as 100° C. to dissolve and disperse the gelator in the solvent.

The above lipid peptide low molecular weight gelator is regarded as being able to complete the gel formation by forming a macro molecular assembly through a weak interaction (van der Waals interaction and the like) between the molecules and destruction of such a molecular assembly hinders the gel formation. Therefore, it is necessary for the gel formation, that a gelator dispersion prepared by heating the solvent at a high temperature be left still while the gelator dispersion is cooled down. When the gelator dispersion is stirred during the cooling down, the gel formation may not be caused.

According to such circumstances, the inventors of the present invention have found an object of providing a material capable of forming a gel under a milder temperature condition, for example, at a temperature of lower than 100° C. and capable of forming a gel even while the gelator dispersion is stirred during cooling down of the dispersion.

For such an object, the inventors of the present invention have studied a method for forming a gel by: dissolving and dispersing temporarily a lipid peptide type compound in a solvent having high solubility of the compound to prepare a solution (dispersion); and blending the solution (dispersion) as what is called a premix of a gelation material in a solvent (such as water).

First, when the inventors of the present invention have studied a solvent having high solubility capable of dissolving a lipid peptide type compound at a high concentration, particularly having high safety by which the use of the solvent for quasi-drugs, cosmetics, and the like is acceptable, they have found that 1,2-alkanediol, 1,3-alkanediol, and ethylene glycol monoalkyl ether are suitable therefor.

Subsequently, when the inventors of the present invention have variously studied for enabling the gel formation using the above premix at a low temperature with stirring, they have found that by blending a polymer emulsifier such as an alginic acid ester in the premix, the solubility and the dispersibility of the premix and the strength of the gel when the premix is blended in a solvent can be secured, and by blending a heat resistance improver such as a fatty acid in the premix, the heat resistance of the formed gel can be improved.

According to the above circumstances, the inventors of the present invention have completed the present invention.

<Dispersion>

The dispersion of the present invention contains a lipid peptide type compound in which a peptide portion having an amino acid repeating bonding structure is bonded to a lipid portion composed of a $C_{9-23}$ aliphatic group, and at least one alcohol selected from the group consisting of 1,2-alkanediol, 1,3-alkanediol, and ethylene glycol monoalkyl ether or a mixed solution of the at least one alcohol.

[Lipid Peptide Type Compound]

In the present invention, the lipid peptide type compound means a low molecular weight compound in which a peptide portion having an amino acid repeating bonding structure is bonded to a lipid portion composed of an aliphatic group.

The lipid peptide type compound used for the dispersion of the present invention has preferably a structure in which the lipid portion is composed of a $C_{9-23}$ aliphatic group.

The lipid peptide type compound used for the dispersion of the present invention has preferably a structure having a plurality of amino acid repeating bonding structures, preferably 2 to 4 amino acid repeating bonding structures, having at a terminal of the compound, a carboxylic acid or a salt thereof, and having at another terminal in the opposite side of the above terminal, a $C_{9-23}$ aliphatic group.

As the lipid peptide type compound in the dispersion of the present invention, more preferably, a compound (lipid peptide) of Formula (1) below to Formula (3) below or a pharmaceutically acceptable salt thereof can be used.

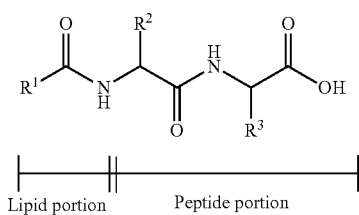

Lipid portion   Peptide portion

In Formula (1), $R^1$ is a $C_{9-23}$ aliphatic group, preferably a straight-chain $C_{11-23}$ aliphatic group optionally having 0 to 2 unsaturated bonds.

Specific examples of the lipid portion (acyl group) composed of $R^1$ and a carbonyl group adjacent to $R^1$ include a lauroyl group, a dodecylcarbonyl group, a myristoyl group, a tetradecylcarbonyl group, a palmitoyl group, a margaroyl group, an oleoyl group, an elaidoyl group, a linoleoyl group, a stearoyl group, a vaccenoyl group, an octadecylcarbonyl group, an arachidoyl group, an eicosylcarbonyl group, a behenoyl group, an erucanoyl group, a docosylcarbonyl group, a lignoceroyl group, and a nervonoyl group, and particularly preferred examples thereof include a lauroyl group, a myristoyl group, a palmitoyl group, a margaroyl group, a stearoyl group, an oleoyl group, an elaidoyl group, and a behenoyl group.

In Formula (1), $R^2$ contained in the peptide portion is a hydrogen atom or a $C_{1-4}$ alkyl group optionally having a $C_{1-2}$ branching chain.

The $C_{1-4}$ alkyl group optionally having a $C_{1-2}$ branching chain means an alkyl group in which the number of carbon atoms of the main chain is 1 to 4 and that may have a $C_{1-2}$ branching chain, and specific examples thereof include a methyl group, an ethyl group, an n-propyl group, an isopropyl group, an n-butyl group, an isobutyl group, a sec-butyl group, and a tert-butyl group.

$R^2$ is preferably a hydrogen atom or a $C_{1-3}$ alkyl group optionally having a $C_1$ branching chain, more preferably a hydrogen atom.

The $C_{1-3}$ alkyl group optionally having a $C_{1-3}$ branching chain means an alkyl group in which the number of carbon atoms of the main chain is 1 to 3 and that may have a $C_1$ branching chain, and specific examples thereof include a methyl group, an ethyl group, an n-propyl group, an isopropyl group, an isobutyl group, and a sec-butyl group, and among them, preferred are a methyl group, an isopropyl group, an isobutyl group, and a sec-butyl group.

In Formula (1), $R^3$ is a $—(CH_2)_n—X$ group. In the $—(CH_2)_n—X$ group, n is a number of 1 to 4 and X is an amino group, a guanidino group, a $—CONH_2$ group, or a 5-membered ring or a 6-membered ring optionally having 1 to 3 nitrogen atom(s), or a fused heterocyclic group composed of a 5-membered ring and a 6-membered ring which optionally have 1 to 3 nitrogen atom(s).

In the $—(CH_2)_n—X$ group as $R^3$, X is preferably an amino group, a guanidino group, a carbamoyl group (a $—CONH_2$ group), a pyrrole group, an imidazole group, a pyrazole group, or an indole group, more preferably an imidazole group. In the $—(CH_2)_n—X$ group, n is preferably 1 or 2, more preferably 1.

Accordingly, the $—(CH_2)_n—$ group is preferably an aminomethyl group, a 2-aminoethyl group, a 3-aminopropyl group, a 4-aminobutyl group, a carbamoylmethyl group, a 2-carbamoylethyl group, a 3-carbamoylbutyl group, a 2-guanidinoethyl group, a 3-guanidinobutyl group, a pyrrolemethyl group, a 4-imidazolemethyl group, a pyrazolemethyl group, or a 3-indolemethyl group, more preferably a 4-aminobutyl group, a carbamoylmethyl group, a 2-carbamoylethyl group, a 3-guanidinobutyl group, a 4-imidazolemethyl group, or a 3-indolemethyl group, further preferably a 4-imidazolemethyl group.

In the compound of Formula (1), as a lipid peptide particularly preferred as the lipid peptide type compound, there can be mentioned the compounds formed from the following lipid portions and peptide portions (amino acid-assembled portion). Here, the abbreviated names of the amino acids are as follows: alanine (Ala); asparagine (Asn); glutamine (Gln); glycine (Gly); histidine (His); isoleucine (Ile); leucine (Leu); lysine (Lys); tryptophan (Trp); and valine (Val).

Examples of the compound include: lauroyl-Gly-His, lauroyl-Gly-Gln, lauroyl-Gly-Asn, lauroyl-Gly-Trp, lauroyl-Gly-Lys, lauroyl-Ala-His, lauroyl-Ala-Gln, lauroyl-Ala-Asn, lauroyl-Ala-Trp, lauroyl-Ala-Lys; myristoyl-Gly-His, myristoyl-Gly-Gln, myristoyl-Gly-Asn, myristoyl-Gly-Trp, myristoyl-Gly-Lys, myristoyl-Ala-His, myristoyl-Ala-Gln, myristoyl-Ala-Asn, myristoyl-Ala-Trp, myristoyl-Ala-Lys; palmitoyl-Gly-His, palmitoyl-Gly-Gln, palmitoyl-Gly-Asn, palmitoyl-Gly-Trp, palmitoyl-Gly-Lys, palmitoyl-Ala-His, palmitoyl-Ala-Gln, palmitoyl-Ala-Asn, palmitoyl-Ala-Trp, palmitoyl-Ala-Lys; stearoyl-Gly-His, stearoyl-Gly-Gln, stearoyl-Gly-Asn, stearoyl-Gly-Trp, stearoyl-Gly-Lys, stearoyl-Ala-His, stearoyl-Ala-Gln, stearoyl-Ala-Asn, stearoyl-Ala-Trp, and stearoyl-Ala-Lys.

Among them, most preferred are lauroyl-Gly-His, lauroyl-Ala-His-myristoyl-Gly-His, myristoyl-Ala-His, palmitoyl-Gly-His, palmitoyl-Ala-His, stearoyl-Gly-His, and stearoyl-Ala-His.

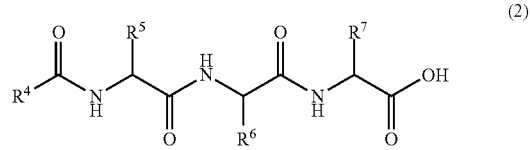

In Formula (2), $R^4$ is a $C_{9-23}$ aliphatic group and preferred specific examples thereof include the same groups as defined with respect to $R^1$ above.

In Formula (2), $R^5$ to $R^7$ are each independently a hydrogen atom, a $C_{1-4}$ alkyl group optionally having a $C_{1-2}$ branching chain, or a $—(CH_2)_n—X$ group and at least one of $R^5$ to $R^7$ is a $—(CH_2)_n—X$ group. n is a number of 1 to 4 and X is an amino group, a guanidino group, a $—CONH_2$ group, or a 5-membered ring or a 6-membered ring optionally having 1 to 3 nitrogen atom(s), or a fused heterocyclic group composed of a 5-membered ring and a 6-membered ring which optionally have 1 to 3 nitrogen atom(s). Here, preferred specific examples of $R^5$ to $R^7$ include the same groups as defined with respect to $R^2$ and $R^3$ above.

In the compound of Formula (2), as a preferred lipid peptide, there can be mentioned the compounds formed from the following lipid portions and peptide portions (amino acid-assembled portion): myristoyl-Gly-Gly-His, myristoyl-Gly-Gly-Gln, myristoyl-Gly-Gly-Asn, myristoyl-Gly-Gly-Trp, myristoyl-Gly-Gly-Lys, myristoyl-Gly-Ala-His, myristoyl-Gly-Ala-Gln, myristoyl-Gly-Ala-Asn, myristoyl-Gly-Ala-Trp, myristoyl-Gly-Ala-Lys, myristoyl-Ala-Gly-His, myristoyl-Ala-Gly-Gln, myristoyl-Ala-Gly-Asn, myristoyl-Ala-Gly-Trp, myristoyl-Ala-Gly-Lys, myristoyl-Gly-His-Gly, myristoyl-His-Gly-Gly, palmitoyl-Gly-Gly-His, palmitoyl-Gly-Gly-Gln, palmitoyl-Gly-Gly-Asn, palmitoyl-Gly-Gly-Trp, palmitoyl-Gly-Gly-Lys, palmitoyl-Gly-Ala-His, palmitoyl-Gly-Ala-Gln, palmitoyl-Gly-Ala-Asn, palmitoyl-Gly-Ala-Trp, palmitoyl-Gly-Ala-Lys, palmitoyl-Ala-Gly-His, palmitoyl-Ala-Gly-Gln, palmitoyl-Ala-Gly-Asn, palmitoyl-Ala-Gly-Trp, palmitoyl-Ala-Gly-Lys, palmitoyl-Gly-His-Gly, and palmitoyl-His-Gly-Gly.

Among them, most preferred are lauroyl-Gly-Gly-His, myristoyl-Gly-Gly-His, palmitoyl-Gly-Gly-His, palmitoyl-Gly-His-Gly, palmitoyl-His-Gly-Gly, and stearoyl-Gly-Gly-His.

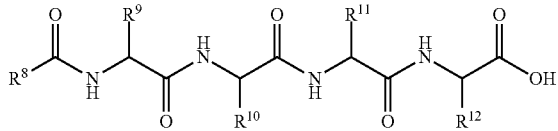

(3)

In Formula (3), $R^8$ is a $C_{9-23}$ aliphatic group and preferred specific examples thereof include the same groups as defined with respect to $R^1$ above.

In Formula (3), $R^9$ to $R^{12}$ are each independently a hydrogen atom, a $C_{1-4}$ alkyl group optionally having a $C_{1-2}$ branching chain, or a —$(CH_2)_n$—X group, and at least one of $R^9$ to $R^{12}$ is a —$(CH_2)_n$—X group. n is a number of 1 to 4 and X is an amino group, a guanidino group, a —$CONH_2$ group, or a 5-membered ring or a 6-membered ring optionally having 1 to 3 nitrogen atom(s), or a fused heterocyclic group composed of a 5-membered ring and a 6-membered ring which optionally have 1 to 3 nitrogen atom(s). Here, preferred specific examples of $R^9$ to $R^{12}$ include the same groups as defined with respect to $R^2$ to $R^3$ above.

Accordingly, in the compound of Formula (3), as a lipid peptide particularly preferred as the preferred lipid peptide type compound, there can be mentioned lauroyl-Gly-Gly-Gly-His, myristoyl-Gly-Gly-Gly-His, palmitoyl-Gly-Gly-Gly-His, palmitoyl-Gly-Gly-His-Gly, palmitoyl-Gly-His-Gly-Gly, palmitoyl-His-Gly-Gly-Gly, and stearoyl-Gly-Gly-Gly-His.

In the present invention, a blending amount of the lipid peptide type compound is, for example 0.01 to 30% by mass, preferably 0.05 to 10% by mass, more preferably 0.1 to 5% by mass, based on the total mass of the obtained hydrogel.

In the present invention, a blending amount of the lipid peptide type compound is, for example 0.1 to 40% by mass, preferably 0.1 to 30% by mass, based on the total mass of the obtained dispersion.

The lipid peptide type compound used in the present invention contains at least one of compounds (lipid peptide) of Formula (1) above to Formula (3) above and pharmaceutically acceptable salts thereof, and when the lipid peptide type compound is used as the hydrogelator, these compounds may be used individually or in combination of two or more thereof.

[Alcohol]

The alcohol used for the dispersion of the present invention is at least one selected from the group consisting of 1,2-alkanediol, 1,3-alkanediol, and ethylene glycol monoalkyl ether.

Specific examples of 1,2-alkanediol include 1,2-pentanediol, 1,2-hexanediol, 1,2-octanediol, and 1,2-decanediol. Among them, preferred are 1,2-pentanediol, 1,2-hexanediol, and 1,2-octanediol, and more preferred are 1,2-pentanediol and 1,2-hexanediol.

Specific examples of 1,3-alkanediol include 2-ethyl-1,3-hexanediol and 1,3,-butanediol. Among them, preferred is 2-ethyl-1,3-hexanediol.

Preferred examples of ethylene glycol monoalkyl ether include alkyl ethers in which the alkyl group is a methyl group, an ethyl group, a propyl group, or a butyl group, that is, ethylene glycol monoethyl ether, ethylene glycol monopropyl ether, and ethylene glycol monobutyl ether. Among them, more preferred are ethylene glycol monopropyl ether and ethylene glycol monobutyl ether.

In the present invention, a blending amount of the alcohol is, for example 1 to 20% by mass, more preferably 2 to 5% by mass, based on the total mass of the obtained hydrogel.

In the present invention, a blending amount of the alcohol is, for example 50% to 90%, more preferably 70% to 90%, based on the total mass of the obtained dispersion. The alcohol used in the present invention is at least one of the alcohols described in the above group of alcohols and these alcohols may be used individually or in combination of two or more thereof.

In the present invention, the dispersion containing the lipid peptide type compound and the alcohol can be suitably used as a thickener for an antifreezing agent.

[Polymer Emulsifier]

Adding a polymer emulsifier to the dispersion of the present invention gives a gel, even when the gelator dispersion is stirred during the gel preparation. As the polymer emulsifier, at least one polymer compound selected from the group consisting of a graft polymer compound produced by grafting a hydrophobic moiety to a hydrophilic backbone and a block polymer compound containing a hydrophobic structural unit and a hydrophilic structural unit may be blended in the dispersion of the present invention.

Examples of the graft polymer compound produced by grafting a hydrophobic moiety to a hydrophilic backbone include xanthan gum, alginic acid esters, and cellulose derivatives.

Examples of the block polymer compound containing a hydrophobic structural unit and a hydrophilic structural unit include copolymers of acrylic acid-alkyl methacrylate.

As the polymer compound, a compound selected from the group consisting of a carboxymethyl cellulose and an alginic acid ester is preferred and propylene glycol alginate is particularly preferred.

In the present invention, a blending amount of the polymer emulsifier is, for example 0.1 to 5% by mass, more preferably 0.2 to 0.5% by mass, based on the total mass of the obtained hydrogel.

In the present invention, a blending amount of the polymer emulsifier is, for example 1.0 to 20.0%, more preferably 1.0 to 10.0%, based on the total mass of the obtained dispersion.

The polymer emulsifier used in the present invention is at least one selected from the group consisting of graft polymer compounds and block polymer compounds and these polymer compounds may be used individually or in combination of two or more thereof.

As the dispersion of the present invention, the dispersion containing the lipid peptide type compound as a gelator and containing in addition to the alcohol, the polymer emulsifier can be suitably used as a premix for preparing a cosmetic or a quasi-drug, that is, as a premix material for preparing a gel used for a cosmetic or a quasi-drug. In addition, in this dispersion (premix), a heat resistance improver and various known additives as an additive for at least one of a cosmetic and a quasi-drug which are described below can also be blended.

The premix can be produced by: adding an alcohol to a lipid peptide type compound to stir the resultant mixture at room temperature or higher and lower than 100° C., preferably 50° C. to 90° C., more preferably 60° C. to 90° C., for example 80° C.; and if desired, adding a heat resistance improver and an additive for at least one of a cosmetic and a quasi-drug to the above mixture to stir the resultant mixture.

[Heat Resistance Improver]

As the heat resistance improver used for the dispersion of the present invention, a fatty acid may be added to the dispersion.

Examples of the fatty acid include a saturated fatty acid, an unsaturated fatty acid, and a salt thereof such as: a straight-chain saturated fatty acid such as caprylic acid, pelargonic acid, capric acid, undecanoic acid, lauric acid, tridecanoic acid, myristic acid, pentadecanoic acid, palmitic acid, margaric acid, stearic acid, nonadecanoic acid, and arachic acid, and a salt thereof; a branched saturated fatty acid such as 2-butyl-5-methylpentanoic acid, 2-isobutyl-5-methylpentanoic acid, dimethyloctanoic acid, dimethylnonanoic acid, 2-butyl-5-methylhexanoic acid, methylundecanoic acid, dimethyldecanoic acid, 2-ethyl-3-methylnonanoic acid, 2,2-dimethyl-4-ethyloctanoic acid, methyldocosanoic acid, 2-propyl-3-methylnonanoic acid, methyltridecanoic acid, dimethyldodecanoic acid, 2-butyl-3-methylnonanoic acid, methyltetradecanoic acid, ethyltridecanoic acid, propyldodecanoic acid, butylundecanoic acid, pentyldecanoic acid, hexylnonanoic acid, 2-(3-methylbutyl)-3-methylnonanoic acid, 2-(2-methylbutyl)-3-methylnonanoic acid, butylethylnonanoic acid, methylpentadecanoic acid, ethyltetradecanoic acid, propyltridecanoic acid, butyldodecanoic acid, pentylundecanoic acid, hexyldecanoic acid, heptylnonanoic acid, dimethyltetradecanoic acid, butylpentylheptanoic acid, trimethyltridecanoic acid, methylhexadecanoic acid, ethylpentadecanoic acid, propyltetradecanoic acid, butyltridecanoic acid, pentyldodecanoic acid, hexylundecanoic acid, heptyldecanoic acid, methylheptylnonanoic acid, dipentylheptanoic acid, methylheptadecanoic acid, ethylhexadecanoic acid, ethylhexadecanoic acid, propylpentadecanoic acid, butyltetradecanoic acid, pentyltridecanoic acid, hexyldodecanoic acid, heptylundecanoic acid, octyldecanoic acid, dimethylhexadecanoic acid, methyloctylnonanoic acid, methyloctadecanoic acid, ethylheptadecanoic acid, dimethylheptadecanoic acid, methyloctyldecanoic acid, methylnonadecanoic acid, methylnonadecanoic acid, dimethyloctadecanoic acid, and butylheptylnonanoic acid, and a salt thereof; a straight-chain monounsaturated fatty acid such as octenoic acid, nonenoic acid, decenoic acid, caproleic acid, undecylenic acid, linderic acid, obtusilic acid, lauroleic acid, tridecenoic acid, tsuzuic acid, myristoleic acid, pentadecenoic acid, hexadecenoic acid, palmitoleic acid, heptadecenoic acid, octadecenoic acid, oleic acid, nonadecenoic acid, and gondoic acid, and a salt thereof; a branched monounsaturated fatty acid such as methylheptenoic acid, methylnonenoic acid, methylundecenoic acid, dimethyldecenoic acid, methyldodecenoic acid, methyltridecenoic acid, dimethyldodecenoic acid, dimethyltridecenoic acid, methyloctadecenoic acid, dimethylheptadecenoic acid, and ethyloctadecenoic acid, and a salt thereof; a straight-chain diunsaturated fatty acid or a straight-chain triunsaturated fatty acid such as linoleic acid, linoelaidic acid, eleostearic acid, linolenic acid, linolenelaidic acid, pseudoeleostearic acid, parinaric acid, and arachidonic acid, and a salt thereof; and an acetylenic acid such as octynoic acid, nonynoic acid, decynoic acid, undecynoic acid, dodecynoic acid, tridecynoic acid, tetradecynoic acid, pentadecynoic acid, heptadecynoic acid, octadecynoic acid, nonadecynoic acid, and dimethyloctadecynoic acid, and a salt thereof.

Examples of the salt of the fatty acid include a sodium salt and a potassium salt thereof.

Among the above fatty acids, preferred is at least one fatty acid selected from the group consisting of a saturated $C_{10-20}$ fatty acid, an unsaturated $C_{10-20}$ fatty acid, and a salt thereof. Preferred examples of the fatty acid include capric acid, undecanoic acid, lauric acid, tridecanoic acid, myristic acid, pentadecanoic acid, palmitic acid, margaric acid, and stearic acid, and more preferred examples thereof include capric acid, lauric acid, myristic acid, palmitic acid, and stearic acid.

Although it has been not yet elucidated in detail how the fatty acid plays a role as a heat resistance improver, for example, when a hydrogel is formed through the gel formation mechanism shown below, the mechanism for the effect expression of the heat resistance improver is expected to be the mechanism shown below.

When the lipid ester type compound is charged into water as the solvent and is dissolved and dispersed in water, lipid portions of two molecules of the lipid ester type compound form with each other, hydrophobically an intermolecular noncovalent bond to form a pair and further, a peptide portion existing in an outer side from the bonding site of the pair in one pair can form with a peptide portion of another pair an intermolecular noncovalent bond through a hydrogen bond. In other words, it is expected that a large number of pairs in which each pair is formed of two molecules of the lipid ester type compound form an assembly thereof through a hydrogen bond of the peptide portion to form what is called a lamellar assembly. It is considered that plural lamellar assemblies are linked with each other to form a network structure and the solvent (water) existing in the network is retained by the peptide portion (hydrophilic) existing in the outer surface of the lamellar assembly, so that the gel state is maintained. However, it is considered that by the elevation of the temperature, the mobility of an alkyl chain of the lipid peptide type compound is enhanced and the peptide portions existing in the outer surface of plural lamellar assemblies approach each other, form a hydrogen bond with each other, and are aggregated with each other; and when consequently, the water existing between plural lamellar assemblies is excluded, the gel state cannot be maintained, so that the lipid peptide type compound is deposited.

At this time, it is considered that by generating electrostatic repulsion between the lamellar assemblies, the approach of plural lamellar assemblies and the formation of the hydrogen bond can be prevented. It is considered that for generating electrostatic repulsion, for example, it is effective to add a compound having a structure that can form a noncovalent bond with a peptide portion existing in the outer surface of one lamellar assembly and does not form a bond with (but generates repulsion to) a peptide portion existing in the outer surface of another lamellar assembly. That is, it is considered that by adding a compound having in the molecule thereof, both a hydrophobic portion and a hydrophilic portion, such as a long-chain fatty acid and a long-chain alcohol, even when the temperature is elevated, the gel state can be stably maintained without generating a deposit in the formed gel.

In the present invention, a blending amount of the heat resistance improver is, for example 0.05 to 0.10% by mass, based on the total mass of the obtained hydrogel.

In the present invention, a blending amount of the heat resistance improver is, for example 0.5 to 2.0%, preferably 0.5 to 1.0%, based on the total mass of the obtained dispersion.

The heat resistance improver used in the present invention is at least one selected from the above group of fatty acids and these fatty acids may be used individually or in combination of two or more thereof.

[Other Additives]

In the composition of the premix, if necessary, an additive generally usable as an additive for cosmetics and an additive for quasi-drugs may be blended. Examples of an adding ingredient of a biologically active substance, a functional substance, and the like which are blended in an external preparation for skin such as cosmetics and quasi-drugs include oleaginous bases, moisturizers, touch improvers, surfactants, polymers, thickening/gelators, solvents, propellants, antioxidants, reducing agents, oxidizing agents, sterilizers, antimicrobe agents, bactericides, chelating agents, pH adjusters, acids, alkalis, powders, inorganic salts, ultraviolet absorbers, whitening agents, vitamins and derivatives thereof, agents for hair growth, blood circulation accelerators, stimulants, hormones, anti-wrinkle agents, anti-aging agents, tightening agents, cold sensing agents, warm sensing agents, wound healing promoters, irritation mitigators, analgesics, cell activators, plant/animal/microbe extracts, antipruritic agents, corneum releasing/dissolving agents, antiperspirants, refrigerants, astringent agents, enzymes, nucleic acids, perfumes, dyestuffs, colorants, dyes, pigments, antiphlogistic agents, antiinflammatory agents, antiasthmatic agents, anti-chronic obstructive pulmonary disease agents, antiallergic agents, immunomodulators, anti-infectious disease agents, and antifungal agents.

These adding ingredients are exemplified as follows.

Preferred examples of the oleaginous base include: higher (polyhydric) alcohols such as cetanol, myristyl alcohol, oleyl alcohol, lauryl alcohol, cetostearyl alcohol, stearyl alcohol, arachyl alcohol, behenyl alcohol, jojoba alcohol, chimyl alcohol, selachyl alcohol, batyl alcohol, hexyldecanol, isostearyl alcohol, 2-octyldodecanol, and dimer diol; aralkyl alcohols and derivatives thereof such as benzyl alcohol; higher fatty acids such as lauric acid, myristic acid, palmitic acid, stearic acid, isostearic acid, behenic acid, undecylenic acid, 12-hydroxystearic acid, palmitoleic acid, oleic acid, linoleic acid, linolenic acid, erucic acid, docosahexaenoic acid, eicosapentaenoic acid, isohexadecanoic acid, anteiso-heneicosanoic acid, long-chain branched fatty acids, dimeric acid, and hydrogenated dimeric acid, and an aluminum salt, a calcium salt, a magnesium salt, a zinc salt, a potassium salt, and a sodium salt of above higher fatty acids which are metal soaps, and an amide of above higher fatty acids which are nitrogen-containing derivatives of above higher fatty acids; hydrocarbons such as liquid paraffin (mineral oil), heavy liquid isoparaffin, light liquid isoparaffin, an α-olefin oligomer, polyisobutene, hydrogenated polyisobutene, polybutene, squalane, squalane derived from olive, squalene, vaseline, and solid paraffin; waxes such as candelilla wax, carnauba wax, rice wax, Japan wax, beeswax, montan wax, ozokerite, ceresin, paraffin wax, microcrystalline wax, petrolatum, Fischer-Tropsch wax, polyethylene wax, and ethylene-propylene copolymer; vegetable oils and fats such as coconut oil, palm oil, palm kernel oil, safflower oil, olive oil, castor oil, avocado oil, sesame oil, tea seed oil, evening primrose oil, wheat germ oil, macadamia nut oil, hazelnut oil, candlenut oil, rose hip oil, meadowfoam oil, persic oil, tea tree oil, peppermint oil, corn oil, rapeseed oil, sunflower oil, wheat germ oil, linseed oil, cotton seed oil, soybean oil, peanut oil, rice bran oil, cacao butter, shea butter, hydrogenated coconut oil, hydrogenated castor oil, jojoba oil, and hydrogenated jojoba oil; animal oils and fats such as beef tallow, milk fat, horse fat, egg yolk oil, mink oil, and turtle oil; animal waxes such as spermaceti wax, lanolin, and orange roughy oil; lanolin such as liquid lanolin, reduced lanolin, adsorptively purified lanolin, lanolin acetate, acetylated lanolin, hydroxylated lanolin, polyoxyethylene lanolin, lanolin fatty acid, hard lanolin fatty acid, lanolin alcohol, acetylated lanolin alcohol, and an acetic acid (cetyl-lanolyl) ester; phospholipids such as lecithin, phosphatidylcholine, phosphatidyl ethanolamine, phosphatidylserine, phosphatidylglycerol, phosphatidylinositol, sphingophospholipids such as sphingomyelin, phosphatidic acid, and lysolecithin; phospholipid derivatives such as hydrogenated soybean phospholipid, partially hydrogenated soybean phospholipid, hydrogenated egg yolk phospholipid, and partially hydrogenated egg yolk phospholipid; sterols such as cholesterol, dihydrocholesterol, lanosterol, dihydrolanosterol, phytosterol, and cholic acid; sapogenin; saponin; sterol esters such as cholesteryl acetate, cholesteryl nonanoate, cholesteryl stearate, cholesteryl isostearate, cholesteryl oleate, di(cholesteryl/behenyl/octyldodecyl) N-lauroyl-L-glutamate, di(cholesteryl/octyldodecyl)N-lauroyl-L-glutamate, di(phytosteryl/behenyl/octyldodecyl)N-lauroyl-L-glutamate, di(phytosteryl/octyldodecyl)N-lauroyl-L-glutamate, acylsarcosine alkyl esters such as isopropyl N-lauroylsarcosinate, cholesteryl 12-hydroxystearate, macadamia nut oil fatty acid cholesteryl, macadamia nut oil fatty acid phytosteryl, phytosteryl isostearate, soft lanolin fatty acid cholesteryl, hard lanolin fatty acid cholesteryl, long-chain branched fatty acid cholesteryl, and long-chain α-hydroxy fatty acid cholesteryl; lipid complexes such as phospholipid-cholesterol complex and phospholipid-phytosterol complex; monoalcohol carboxylic acid esters such as octyldodecyl myristate, hexyldecyl myristate, octyldodecyl isostearate, cetyl palmitate, octyldodecyl palmitate, cetyl octanoate, hexyldecyl octanoate, isotridecyl isononanoate, isononyl isononanoate, octyl isononanoate, isotridecyl isononanoate, isodecyl neopentanoate, isotridecyl neopentananoate, isostearyl neopentanoate, octyldodecyl neodecanoate, oleyl oleate, octyldodecyl oleate, octyldodecyl ricinoleate, lanolin fatty acid octyldodecyl, hexyldecyl dimethyloctanoate, octyldodecyl erucate, hydrogenated castor oil isostearate, ethyl oleate, avocado oil fatty acid ethyl, isopropyl myristate, isopropyl palmitate, octyl palmitate, isopropyl isostearate, lanolin fatty acid isopropyl, diethyl sebacate, diisopropyl sebacate, dioctyl sebacate, diisopropyl adipate, dibutyloctyl sebacate, diisobutyl adipate, dioctyl succinate, and triethyl citrate; oxy acid esters such as cetyl lactate, diisostearyl malate, and hydrogenated castor oil monoisostearate; polyhydric alcohol fatty acid esters such as glyceryl trioctanoate, glyceryl trioleate, glyceryl triisostearate, glyceryl diisostearate, glyceryl tri(caprylate/caprinate), glyceryl tri(caprylate/caprinate/myristate/stearate), hydrogenated rosin glyceride (hydrogenated ester gum), rosin triglyceride (ester gum), glyceryl behenate/eicosanedioate, trimethylolpropane trioctanoate, trimethylolpropane triisostearate, neopentyl glycol dioctanoate, neopentyl glycol dicaprinate, 2-butyl-2-ethyl-1,3-propanediol dioctanoate, propylene glycol dioleate, pentaerythrityl tetraoctanoate, hydrogenated rosin pentaerythrityl, ditrimethylolpropane triethylhexanoate, ditrimethylolpropane (isostearate/sebacate), pentaerythrityl triethylhexanoate, dipentaerythrityl (hydroxystearate/stearate/rosinate), diglyceryl diisostearate, polyglyceryl tetraisostearate, polyglyceryl-10 nonaisostearate, polyglyceryl-8 deca(erucate/isostearate/ricinoleate), diglyceryl oligoester of (hexyldecanoic acid/sebacic acid), glycol distearate (ethylene glycol distearate), 3-methyl-1,5-pentanediol dineopentanoate, and 2,4-diethyl-1,5-pentanediol dineopentanoate; derivatives of dimer acids or dimer diols such as diisopropyl dimer-dilinoleate, diisostearyl dimer-dilinoleate, di(isostearyl/phytosteryl) dimer-dilinoleate, (phytosteryl/behenyl) dimer-dilinoleate, (phytosteryl/isostearyl/cetyl/stearyl/behenyl) dimer-dilinoleate, dimer-dilinoleyl dimer-dilinoleate, dimer-dilinoleyl diisostearate, dimer-dilinoleyl-hydrogenated rosin condensate, hydrogenated castor oil dimer-dilinoleate, and hydroxyalkyl dimer-dilinoleyl ether; fatty acid alkanolamides such as coconut oil fatty acid monoethanolamide (cocamide MEA), coconut oil fatty acid diethanolamide (cocamide DEA), lauric acid monoethanolamide (lauramide MEA), lauric acid diethanolamide (lauramide DEA), lauric acid monoisopropanolamide (lauramide MIPA), palmitic acid monoethanolamide (paltamide MEA), palmitic acid diethanolamide (paltamide DEA), and coconut oil fatty acid methylethanolamide (cocamidemethyl MEA); silicones such as dimethicone (dimethylpolysiloxane), dimethicone having high degree of polymerization (dimethyl polysiloxane having high degree of polymerization), cyclomethicone (cyclic dimethylsiloxane, decamethylcyclopentasiloxane), phenyl trimethicone, diphenyl dimethicone, phenyl dimethicone, stearoxypropyldimethylamine, a (aminoethylaminopropyl methicone/dimethicone) copolymer, dimethiconol, a dimethiconol crosspolymer, a silicone resin, a silicone rubber, amino-modified silicone such as aminopropyl dimethicone and amodimethicone, cation-modified silicone, polyether-modified silicone such as dimethicone copolyol, polyglycerin-modified silicone, sugar-modified silicone, carboxylic acid-modified silicone, phosphoric acid-modified silicone, sulfuric acid-modified silicone, alkyl-modified silicone, fatty acid-modified silicone, alkyl ether-modified silicone, amino acid-modified silicone, peptide-modified silicone, fluorine-modified silicone, cation-modified and polyether-modified silicone, amino-modified and polyether-modified silicone, alkyl-modified and polyether-modified silicone, and polysiloxane-oxyalkylene copolymer; and fluorine-based oil solutions such as perfluorodecane, perfluorooctane, and perfluoropolyether.

Preferred examples of the moisturizer and the touch improver include: polyols such as glycerin, 1,3-butylene glycol, propylene glycol, 3-methyl-1,3-butanediol, 1,3-propanediol, 2-methyl-1,3-propanediol, trimethylolpropane, pentaerythritol, hexylene glycol, diglycerin, polyglycerin, diethylene glycol, polyethylene glycol, dipropylene glycol, polypropylene glycol, and ethylene glycol-propylene glycol copolymer, and polymers of these polyols; glycol alkyl ethers such as diethylene glycol monoethyl ether (ethoxy diglycol), ethylene glycol monoethyl ether, ethylene glycol monobutyl ether, and diethylene glycol dibutyl ether; water soluble esters such as polyglyceryl-10 (eicosanedienoate/tetradecanedienoate) and polyglyceryl-10 tetradecanedienoate; sugar alcohols such as sorbitol, xylitol, erythritol, mannitol, and maltitol; saccharides such as glucose, fructose, galactose, mannose, threose, xylose, arabinose, fucose, ribose, deoxyribose, maltose, trehalose, lactose, raffinose, gluconic acid, glucuronic acid, cyclodextrins (α-cyclodextrin, β-cyclodextrin, γ-cyclodextrin, and modified cyclodextrin such as maltosylated cyclodextrin and hydroxyalkylated cyclodextrin), β-glucan, chitin, chitosan, heparin and derivatives thereof, pectin, arabinogalactan, dextrin, dextran, glycogen, ethyl glucoside, and polymers or copolymers of glucosylethyl methacrylate, and derivatives of these saccharides; hyaluronic acid and sodium hyaluronate; sodium chondroitin sulfate; mucoitinsulfuric acid, charonin sulfate, keratosulfate, and dermatan sulfate; *Tremella fuciformis* extracts and *Tremella fuciformis* polysaccharides; fucoidan; tuberosa polysaccharides or natural polysaccharides; organic acids such as citric acid, tartaric acid, and lactic acid, and salts thereof; urea and derivatives thereof; 2-pyrrolidone-5-carboxylic acid and salts thereof such as a sodium salt; amino acids such as betaine (trimethylglycine), proline, hydroxyproline, alginine, lysine, serine, glycine, alanine, phenylalanine, tyrosine, β-alanine, threonine, glutamic acid, glutamine, asparagine, aspartic acid, cysteine, cysteine, methionine, leucine, isoleucine, valine, tryptophan, histidine, and taurine, and salts of these amino acids; protein peptides such as collagen, fish-derived collagen, atelocollagen, gelatin, elastin, collagen decomposed peptide, hydrolyzed collagen, hydroxypropylammonium chloride-hydrolyzed collagen, elastin decomposed peptide, keratin decomposed peptide, hydrolyzed keratin, conchiolin decomposed peptide, hydrolyzed conchiolin, silk protein decomposed peptide, hydrolyzed silk, lauroyl-hydrolyzed silk sodium, soybean protein decomposed peptide, wheat protein decomposed peptide, hydrolyzed wheat protein, casein decomposed peptide, and acylated peptide, and derivatives of these protein peptides; acylated peptides such as palmitoyl oligopeptide, palmitoyl pentapeptide, and palmitoyl tetrapeptide; silylated peptides; a culture solution for lactic acid bacterium, yeast extract, eggshell membrane protein, cow submaxillary gland mucin, hypotaurine, sesame lignan glycoside, glutathione, albumin, and milk serum; choline chloride and phosphorylcholine; animal/plant extracted components such as placenta extract, elastin, collagen, aloe extract, hamamelis water, sponge cucumber water, chamomilla extract, licorice extract, comfrey extract, silk extract, chestnut rose extract, yarrow extract, eucalyptus extract, and melilot extract, ceramides such as natural ceramide (type 1, 2, 3, 4, 5, 6), hydroxyceramide, pseudo-ceramide, sphingoglycolipid, and extracts containing ceramide or ceramide saccharide.

Preferred examples of the surfactant include anionic surfactants, nonionic surfactants, cationic surfactants, amphoteric surfactants, and polymer surfactants. Preferred examples of the surfactant are as follows. Preferred examples of the anionic surfactant include: salts of fatty acids such as potassium laurate and potassium myristate; alkyl sulfates such as sodium lauryl sulfate, triethanolamine lauryl sulfate, and ammonium lauryl sulfate; polyoxyethylene alkyl sulfates such as sodium laureth sulfate and triethanolamine laureth sulfate; salts of acyl-N-methylamino acids such as sodium cocoylmethyl taurate, potassium cocoylmethyl taurate, sodium lauroylmethyl taurate, sodium myristoylmethyl taurate, sodium lauroylmethyl alaninate, sodium lauroyl sarcosinate, triethanolamine lauroyl sarcosinate, and sodium methylalanine lauroyl glutamate; salts of acylamino acids such as sodium cocoyl glutamate, triethanolamine cocoyl glutamate, sodium lauroyl glutamate, sodium myristoyl glutamate, sodium stearoyl glutamate, ditriethanolamine palmitoyl aspartate, and triethanolamine cocoyl alaninate; polyoxyethylene alkyl ether acetates such as sodium laureth acetate; succinic acid ester salts such as sodium lauroylmonoethanolamide succinate; fatty acid alkanolamide ether carboxylates; acyl lactates; polyoxyethylene aliphatic amine sulfates; fatty acid alkanolamide sulfates; fatty acid glyceride sulfates such as glycerin hydrogenated coconut oil fatty acid sulfate sodium salt; alkylbenzene polyoxyethylene sulfates; olefin sulfonates such as sodium α-olefin sulfonate; alkyl sulfosuccinates such as disodium lauryl sulfosuccinate and sodium dioctylsulfosuccinate; alkyl ether sulfosuccinates such as disodium laureth sulfosuccinate, sodium monolauroyl monoethanolamide polyoxyethylene sulfosuccinate, and sodium lauryl polypropylene glycol sulfosuccinate; alkyl benzene sulfonates such as sodium tetradecylbenzenesulfonate and triethanolamine tetradecylbenzenesulfonate; alkylnaphthalenesulfonates; alkanesulfonates; methyl ester salts of α-sulfo fatty acids; acylisethionic acid salts; alkyl glycidyl ether sulfonates; alkyl sulfo acetates; alkyl ether phosphates such as sodium laureth phosphate, sodium dilaureth phosphate, sodium trilaureth phosphate, and sodium monooleth phosphate; alkyl phosphates such as potassium lauryl phosphate; sodium caseinate; alkyl aryl ether phosphates; fatty amide ether phosphates; phospholipids such as phosphatidylglycerol, phosphatidylinositol, and phosphatidic acid; silicone-based anion surfactants such as carboxylic acid-modified silicone, phosphoric acid-modified silicone, and sulfuric acid-modified silicone. Preferred examples of the nonionic surfactant include: polyoxyethylene alkyl ethers having various numbers of added molecules of polyoxyethylene such as laureth (polyoxyethylene lauryl ether) group, ceteth (polyoxyethylene cetyl ether) group, steareth (polyoxyethylene stearyl ether) group, beheneth (polyoxyethylene behenyl ether) group, isosteareth (polyoxyethylene isostearyl ether) group, and octyldodeceth (polyoxyethylene octyldodecyl ether) group; polyoxyethylene alkyl phenyl ethers; derivatives of castor oil and hydrogenated castor oil such as polyoxyethylene hydrogenated castor oil, polyoxyethylene castor oil, polyoxyethylene hydrogenated castor oil monoisostearate, polyoxyethylene hydrogenated castor oil triisostearate, polyoxyethylene hydrogenated castor oil monopyroglutamate-monoisostearate-diester, and polyoxyethylene hydrogenated castor oil maleate; polyoxyethylene phytosterol; polyoxyethylene cholesterol; polyoxyethylene cholestanol; polyoxyethylene lanolin; polyoxyethylene reduced lanolin; polyoxyethylene-polyoxypropylene alkyl ethers such as polyoxyethylene-polyoxypropylene cetyl ether, polyoxyethylene-polyoxypropylene 2-decyltetradecyl ether, polyoxyethylene-polyoxypropylene monobutyl ether, polyoxyethylene-polyoxypropylene hydrogenated lanolin; polyoxyethylene-polyoxypropylene glycerin ether, and polyoxyethylene-polyoxypropylene glycol; (poly)glycerin polyoxypropylene glycols such as PPG-9 diglyceryl; glycerin fatty acid partial esters such as glyceryl stearate, glyceryl isostearate, glyceryl palmitate, glyceryl myristate, glyceryl oleate, glyceryl coconut oil fatty acid ester, glycerin mono cottonseed oil fatty acid ester, glyceryl monoerucate, glyceryl sesquioleate, glycerin ester of α,α'-oleic acid-pyroglutamic acid, and glyceryl monostearate malic acid; polyglycerin fatty acid esters such as polyglyceryl-2,3,4,5, 6,8, or 10 stearate, polyglyceryl-6 or 10 distearate, polyglyceryl-2 tristearate, polyglyceryl-10 decastearate, polyglyceryl-2,3,4,5,6,8, or 10 isostearate, polyglyceryl-2 diisostearate (diglyceryl diisostearate), polyglyceryl-3 diisostearate, polyglyceryl-10 diisostearate, polyglyceryl-2 triisostearate, polyglyceryl-2 tetraisostearate, polyglyceryl-10 decaisostearate, polyglyceryl-2,3,4,5,6,8, or 10 oleate, polyglyceryl-6 dioleate, polyglyceryl-2 trioleate, and polyglyceryl-10 decaoleate; ethylene glycol mono fatty acid ester such as ethylene glycol monostearate; propylene glycol mono fatty acid ester such as propylene glycol monostearate; pentaerythritol fatty acid partial ester; sorbitol fatty acid partial ester; maltitol fatty acid partial ester; maltitol ether; sorbitan fatty acid ester such as sorbitan monooleate, sorbitan monoisostearate, sorbitan monolaurate, sorbitan monopalmitate, sorbitan monostearate, sorbitan sesquioleate, sorbitan trioleate, diglycerol sorbitan penta-2-ethylhexylate, and diglycerol sorbitan tetra-2-ethylhexylate; saccharide derivative partial esters such as sucrose fatty acid ester, methylglucoside fatty acid ester, and trehalose undecylate; alkyl glucoside such as caprylyl glucoside; alkylpolyglucoside; lanolin alcohol; reduced lanolin; polyoxyethylene fatty acid mono- and di-ester such as polyoxyethylene distearate, polyoxyethylene diisostearate, polyoxyethylene monooleate, and polyoxyethylene dioleate; polyoxyethylene propylene glycol fatty acid ester; polyoxyethylene glycerin fatty acid ester such as polyoxyethylene monooleate such as polyoxyethylene glycerin monostearate, polyoxyethylene glycerin monoisostearate, and polyoxyethylene glycerin triisostearate; polyoxyethylene sorbitan fatty acid ester such as polyoxyethylene sorbitan monooleate, polyoxyethylene sorbitan monostearate, polyoxyethylene sorbitan monooleate, and polyoxyethylene sorbitan tetraoleate; polyoxyethylene sorbitol fatty acid ester such as polyoxyethylene sorbitol monolaurate, polyoxyethylene sorbitol monooleate, polyoxyethylene sorbitol pentaoleate, and polyoxyethylene sorbitol monostearate; polyoxyethylene methylglucoside fatty acid ester; polyoxyethylene alkyl ether fatty acid ester; polyoxyethylene animal and vegetable oils and fats such as polyoxyethylene sorbitol beeswax; alkyl glyceryl ethers such as isostearyl glyceryl ether, chimyl alcohol, selachyl alcohol, and batyl alcohol; polyhydric alcohol alkyl ether; polyoxyethylene alkylamine; tetrapolyoxyethylene/tetrapolyoxypropylene-ethylenediamine condensates; nature-originated surfactants such as saponin and sophorolipid; polyoxyethylene fatty acid amide; fatty acid alkanolamides such as coconut oil fatty acid monoethanolamide (cocamide MEA), coconut oil fatty acid diethanolamide (cocamide DEA), lauric acid monoethanolamide (lauramide MEA), lauric acid diethanolamide (lauramide DEA), lauric acid monoisopropanolamide (lauramide MIPA), palmitic acid monoethanolamide (paltamide MEA), palmitic acid diethanolamide (paltamide DEA), and coconut oil fatty acid methylethanolamide (cocamide methyl MEA); alkyldimethylamine oxides such as lauramine oxide, cocamine oxide, stearamine oxide, and behenamine oxide; alkylethoxydimethylamine oxides; polyoxyethylene alkyl mercaptans; polyether-modified silicones such as dimethicone copolyol; and silicone-based nonionic surfactants such as polysiloxane-oxyalkylene copolymers, polyglycerin-modified silicone, and saccharide-modified silicone. Preferred examples of the cationic surfactant include: alkyltrimethylammonium chlorides such as behentrimonium chloride, steartrimonium chloride, cetrimonium chloride, and lauryltrimonium chloride; alkyltrimethylammonium bromides such as steartrimonium bromide; dialkyldimethylammonium chlorides such as disteardimonium chloride and dicocodimonium chloride; fatty acid amido amines such as stearamidopropyl dimethylamine and stearamidoethyl diethylamine, and salts thereof; alkyletheramines such as stearoxypropyl dimethylamine, and salts or quaternary salts thereof; fatty acid amide-type quaternary ammonium salts such as long-chain branched fatty acid (12 to 31) aminopropylethyldimethylammonium ethyl sulfate and lanolin fatty acid aminopropylethyldimethylammonium ethyl sulfate; polyoxyethylene alkylamines and salts or quaternary salts thereof; alkylamine salts; fatty acid amide guanidium salt; alkyl ether ammonium salts; alkyl trialkylene glycol ammonium salts; benzalkonium salts; benzethonium salts; pyridinium salts such as cetylpyridinium chloride; imidazolinium salts; alkyl isoquinolinium salts; dialkyl morpholinium salts; polyamine fatty acid derivatives; and silicone-based cationic surfactants such as amino-modified silicone such as aminopropyl dimethicone and amodimethicone, cation-modified silicone, cation-modified and polyether-modified silicone, and amino-modified and polyether-modified silicone. Preferred examples of the amphoteric surfactant include: N-alkyl-N,N-dimethyl amino acid betaines such as lauryl betaine (lauryldimethyl aminoacetic acid betaine); fatty acid amide alkyl-N,N-dimethyl amino acid betaines such as cocamidopropyl betaine and lauramidopropyl betaine; imidazoline-type betaines such as sodium cocoamphoacetate and sodium lauroamphoacetate; alkylsulfo betaines such as alkyl dimethyl taurine; sulfuric acid-type betaines such as alkyl dimethyl amino ethanol sulfuric acid ester; phosphoric acid-type betaines such as alkyl dimethyl amino ethanol phosphoric acid ester; phospholipids such as sphingophospholipids such as phosphatidylcholine, phosphatidyl ethanolamine, phosphatidylserine, and sphingomyelin, lysolecithin, hydrogenated soybean phospholipid, partially hydrogenated soybean phospholipid, hydrogenated egg yolk phospholipid, partially hydrogenated egg yolk phospholipid, and lecithin hydroxide; and silicone-based amphoteric surfactants. Preferred examples of the polymer surfactant include polyvinyl alcohols, sodium alginate, starch derivatives, tragacanth gum, copolymers of acrylic acid-alkyl methacrylate, and various silicone-based surfactants.

Preferred examples of the polymer, the thickener, and the gelator include: guar gum; locust bean gum; quince seed; carrageenan; galactan; gum arabic; tara gum; tamarind; furcellaran; karaya gum; sunset hibiscus; cara gum; tragacanth gum; pectin; pectic acid and salts such as a sodium salt thereof; alginic acid and salts such as a sodium salt thereof; mannan; starches of rice, corn, potato, and wheat; xanthan gum; dextran; succinoglucan; curdlan; hyaluronic acid and salts thereof; xanthan gum; pullulan, gellan gum; chitin; chitosan; agar; brown alga extract; chondroitin sulfate salt; casein; collagen; gelatin; albumin; celluloses and derivatives thereof such as methyl cellulose, ethyl cellulose, hydroxyethyl cellulose, hydroxypropyl cellulose, hydroxypropylmethyl cellulose, carboxymethyl cellulose and salts such as a sodium salt thereof, methylhydroxypropyl cellulose, sodium cellulose sulfate, dialkyldimethyl ammonium sulfate cellulose, crystalline cellulose, and powdered cellulose; starch polymers such as soluble starch, carboxymethyl starch, methylhydroxypropyl starch, and methyl starch; starch derivatives such as starch hydroxypropyltrimonium chloride, and aluminum corn starch octenylsuccinate; alginic acid derivatives such as sodium alginate and propylene glycol alginate ester; polyvinylpyrrolidone (PVP); polyvinylalcohol (PVA); vinylpyrrolidone-vinylalcohol copolymers; polyvinyl methyl ether; polyethylene glycol; polypropylene glycol; polyoxyethylene-polyoxypropylene copolymers; amphoteric methacrylate ester copolymers such as (methacryloyloxyethylcarboxybetaine/alkyl methacrylate) copolymer and (acrylates/stearyl acrylate/ethylamine oxide methacrylate) copolymer; (dimethicone/vinyldimethicone) cross polymers; (alkyl acrylate/diacetoneacrylamide) copolymer and AMP-(alkyl acrylate/diacetoneacrylamide) copolymer; polyvinyl acetate partially saponified products; maleic acid polymers; vinylpyrrolidone-dialkylaminoalkyl methacrylate copolymers; acrylic resin alkanolamines; polyesters and water-dispersible polyesters; polyacrylamides; copolymers of polyacrylate ester such as ethyl polyacrylate; carboxyvinyl polymers; polyacrylic acid and salts such as a sodium salt thereof; copolymers of acrylic acid-methacrylate ester; copolymers of acrylic acid-alkyl methacrylate; cationized celluloses such as polyquaternium-10; diallyldimethylammonium chloride-acrylamide copolymers such as polyquaternium-7; acrylic acid-diallyldimethylammonium chloride copolymers such as polyquaternium-22; acrylic acid-diallyldimethylammonium chloride-acrylamide copolymers such as polyquaternium-39; copolymers of acrylic acid-cationized methacrylate ester; copolymers of acrylic acid-cationized methacrylamide; acrylic acid-methyl acrylate-methacrylamidepropyltrimethylammonium chloride copolymers such as polyquaternium-47; methacryloyl chloride choline ester polymers; cationized polysaccharides such as cationized oligosaccharides, cationized dextran; guar hydroxypropyltrimonium chloride; polyethyleneimines; cation polymers; polymers of 2-methacryloyloxyethyl phosphorylcholine such as polyquaternium-51, and copolymers thereof with a butyl methacrylate-copolymer; polymer emulsions such as an acrylic resin emulsion, an ethyl polyacrylate emulsion, a polyacrylalkyl ester emulsion, a polyvinyl acetate resin emulsion, a natural rubber latex, and a synthetic latex; nitrocelluloses; polyurethanes and various copolymers; various silicones; various silicone-based copolymers such as an acryl-silicone graft copolymer; various fluorine-based polymers; 12-hydroxystearic acid and salts thereof; dextrin fatty acid esters such as dextrin palmitate and dextrin myristate; silicic anhydride and fumed silica (ultrafine particle silicic anhydride); magnesium aluminum silicate and magnesium sodium silicate; metal soaps; dialkylphosphoric acid metal salts; bentonite; hectorite; organic modified clay minerals; saccharose fatty acid esters; and fructo-oligosaccharide fatty acid esters. Among the above examples, preferred are celluloses and derivatives thereof, alginic acid and salts thereof, polyvinyl alcohols, hyaluronic acid and salts thereof, and collagen.

Preferred examples of the solvent and the propellant include: lower alcohols such as ethanol, 2-propanol (isopropyl alcohol), butanol, and isobutyl alcohol; glycols such as propylene glycol, 1,3-butylene glycol, diethylene glycol, dipropylene glycol, and isopentyl diol; glycol ethers such as diethylene glycol monoethyl ether (ethoxy diglycol), ethylene glycol monoethyl ether, ethylene glycol monobutyl ether, triethylene glycol monoethyl ether, diethylene glycol diethyl ether, diethylene glycol dibutyl ether, propylene glycol monoethyl ether, and dipropylene glycol monoethyl ether; glycol ether esters such as ethylene glycol monoethyl ether acetate, diethylene glycol monoethyl ether acetate, and propylene glycol monoethyl ether acetate; glycol esters such as diethoxyethyl succinate and ethylene glycol disuccinate; benzyl alcohol; benzyloxyethanol; propylene carbonate; dialkyl carbonate; acetone; ethyl acetate; N-methylpyrrolidone; toluene; and propellants such as fluorocarbon, fron gas for the next generation, LPG, dimethyl ether, and carbon dioxide.

Preferred examples of the antioxidant include: tocopherol derivatives such as tocopherol (vitamin E) and tocopherol acetate; BHT and BHA; gallic acid derivatives such as propyl gallate; at least one of vitamin C (ascorbic acid) and derivative thereof; erythorbic acid and derivatives thereof;

sulfites such as sodium sulfite; hydrogensulfites such as sodium hydrogensulfite; thiosulfates such as sodium thiosulfate; metabisulfites; thiotaurine and hypotaurine; thioglycerol, thiourea, and thioglycolic acid; and cysteine hydrochloride.

Preferred examples of the reducing agent include thioglycolic acid, cysteine, and cysteamine.

Preferred examples of the oxidizing agent include hydrogen peroxide water, ammonium persulfate, sodium bromate, and percarbonic acid.

Preferred examples of the sterilizer, the antimicrobe agent, and the bactericide include: hydroxybenzoic acid and salts thereof or esters thereof such as methylparaben, ethylparaben, propylparaben, and butylparaben; salicylic acid; sodium benzoate; phenoxy ethanol; isothiazolinone derivatives such as methyl-chloro-isothiazolinone and methyl-isothiazolinone; imidazolinium urea; dehydroacetic acid and salts thereof; phenols; halogenated bisphenols such as triclosan; acid amides; quaternary ammonium salts; trichlorocarbanilide; zinc pyrithione; benzalkonium chloride; benzethoniumu chloride; sorbic acid, chlorohexidine; chlorohexidine glucanate; halocarban; hexachlorophene; hinokitiol; phenols other than the above phenols such as phenol, isopropylphenol, cresol, thymol, p-chlorophenol, phenylphenol, and sodium phenylphenate; phenylethyl alcohol; photosensitive elements; antibacterial zeolite; and silver ion.

Preferred examples of the chelating agent include: edetates (ethylenediaminetetraacetates) such as EDTA, EDTA2Na, EDTA3Na, and EDTA4Na; hydroxyethylethylenediaminetriacetates such as HEDTA3Na; pentetates (diethylenetriaminepentaacetates); phytic acid; phosphonic acids such as etidronic acid, and salts such as a sodium salt thereof; sodium oxalate; polyamino acids such as polyaspartic acid and polyglutamic acid; sodium polyphosphate, sodium metaphosphate, and phosphoric acid; sodium citrate and citric acid; alanine; dihydroxyethylglycine; gluconic acid; ascorbic acid; succinic acid; and tartaric acid.

Preferred examples of the pH adjuster, the acid, and the alkali include citric acid, sodium citrate, lactic acid, sodium lactate, potassium lactate, glycolic acid, succinic acid, acetic acid, sodium acetate, malic acid, tartaric acid, fumaric acid, phosphoric acid, hydrochloric acid, sulfuric acid, monoethanolamine, diethanolamine, triethanolamine, isopropanolamine, triisopropanolamine, 2-amino-2-methyl-1,3-propandiol, 2-amino-2-hydroxymethyl-1,3-propanediol, arginine, sodium hydroxide, potassium hydroxide, ammonia water, guanidine carbonate, and ammonium carbonate.

Preferred examples of the powder include: inorganic powders having various sizes and shapes such as mica, talc, kaolin, sericite, montmorillonite, kaolinite, isinglass, muscovite, phlogopite, synthetic isinglass, lepidolite, biotite, vermiculite, magnesium carbonate, calcium carbonate, aluminum silicate, barium silicate, potassium silicate, magnesium silicate, strontium silicate, a metal salt of tangstic acid, magnesium, zeolite, barium sulfate, baked calcium sulfate, calcium phosphate, fluoroapatite, hydroxyapatite, a ceramic powder, bentonite, smectite, clay, mud, metal soap (for example, zinc myristate, calcium palmitate, aluminum stearate), calcium carbonate, red iron oxide, yellow iron oxide, black iron oxide, ultramarine, Prussian blue, carbon black, titanium oxide, fine particle or ultrafine particle titanium oxide, zinc oxide, fine particle or ultrafine particle zinc oxide, alumina, silica, fumed silica (ultrafine particle silicic anhydride), mica titanium, fish scale guanine, boron nitride, a photochromic pigment, synthetic fluorophlogopite, a fine particle compound powder, gold, and aluminum; inorganic powders which are powders hydrophobized or hydrophilized by subjecting the above inorganic powders to a treatment using various surface treating agent such as a silicone such as a hydrogen silicone and a cyclic hydrogen silicone, another silane, or a titanium coupling agent; organic powders having various sizes and shapes such as starch, cellulose, a nylon powder, a polyethylene powder, a poly(methyl methacrylate) powder, a polystyrene powder, a powder of a copolymer resin of styrene and acrylic acid, a polyester powder, a benzoguanamine resin powder, a powder in which polyethylene terephthalate and poly(methyl methacrylate) are layered, a powder in which polyethylene terephthalate, aluminum, and epoxy are layered, a urethane powder, a silicone powder, and a Teflon (registered trademark) powder, and surface treated powders; and organic-inorganic compound powders.

Preferred examples of the inorganic salt include: sodium chloride-containing salts such as a salt, a crude salt, a rock salt, a sea salt, and a natural salt; potassium chloride, aluminum chloride, calcium chloride, magnesium chloride, bittern, zinc chloride, and ammonium chloride; sodium sulfate, aluminum sulfate, aluminum potassium sulfate (alum), aluminum ammonium sulfate, barium sulfate, calcium sulfate, potassium sulfate, magnesium sulfate, zinc sulfate, iron sulfate, and copper sulfate; and sodium phosphates such as monosodium dihydrogen phosphate, disodium hydrogen phosphate, and trisodium phosphate, potassium phosphates, calcium phosphates, and magnesium phosphates.

Preferred examples of the ultraviolet absorber include: benzoic acid-based ultraviolet absorbers such as p-aminobenzoic acid, p-aminobenzoic acid monoglycerin ester, N,N-dipropoxy-p-aminobenzoic acid ethyl ester, N,N-diethoxy-p-aminobenzoic acid ethyl ester, N,N-dimethyl-p-aminobenzoic acid ethyl ester, N,N-dimethyl-p-aminobenzoic acid butyl ester, and N,N-dimethyl-p-aminobenzoic acid ethyl ester; anthranilic acid-based ultraviolet absorbers such as homomenthyl-N-acetylanthranilate; salicylic acid-based ultraviolet absorbers such as salicylic acid and sodium salt thereof amyl salicylate, menthyl salicylate, homomenthyl salicylate, octyl salicylate, phenyl salicylate, benzyl salicylate, and p-isopropanolphenyl salicylate; cinnamic acid-based ultraviolet absorbers such as octyl cinnamate, ethyl 4-isopropyl-cinnamate, methyl 2,5-diisopropyl-cinnamate, ethyl 2,4-diisopropy-cinnamate, methyl 2,4-diisopropyl-cinnamate, propyl p-methoxycinnamate, isopropyl p-methoxycinnamate, isoamyl p-methoxycinnamate, 2-ethylhexyl p-methoxycinnamate (octyl p-methoxycinnamate), 2-ethylethyl p-methoxycinnamate (cinoxate), cyclohexyl p-methoxycinnamate, ethyl α-cyano-β-phenyl-cinnamate, 2-ethylhexyl α-cyano-β-phenylcinnamate (octocrylene), glyceryl mono-2-ethylhexanoyl-di-p-methoxycinnamate, and ferulic acid and derivatives thereof benzophenone-based ultraviolet absorbers such as 2,4-dihydroxybenzophenone, 2,2'-dihydroxy-4-methoxybenzophenone, 2,2'-dihydroxy-4,4'-dimethoxybenzophenone, 2,2',4,4'-tetrahydroxybenzophenone, 2-hydroxy-4-methoxybenzophenone (oxybenzone-3), 2-hydroxy-4-methoxy-4'-methylbenzophenone, 2-hydroxy-4-methoxybenzophenone 5-sulfonate, 4-phenylbenzophenone, 2-ethylhexyl-4'-phenyl-benzophenone 2-carboxylate, 2-hydroxy-4-n-octoxybenzophenone, and 4-hydroxy-3-carboxybenzophenon; 3-(4'-methylbenzylidene)-d,l-camphor; 3-benzylidene-d,l-camphor; 2-phenyl-5-methylbenzoxazole; 2,2'-hydroxy-5-methylphenyl-benzotriazole; 2-(2'-hydroxy-5'-t-octyphenyl)benzotriazole; 2-(2'-hydroxy-5'-methylphenyl)benzotriazole; dibenzalazine; dianisoylmethane; 5-(3,3-dimethyl-2-norbornylidene)-

3-pentan-2-one; dibenzoylmethane derivatives such as 4-t-butylmethoxydibenzoylmethane; octyltriazone; urocanic acid derivatives such as urocanic acid and ethyl urocanate; 2-(2'-hydroxy-5'-methylphenyl)benzotriazole; 1-(3,4-dimethoxyphenyl)-4,4-dimethyl-1,3-pentanedione; hydantoin derivatives such as 2-ethylhexyl dimethoxybenzylidene dioxoimidazolidine propionate; phenylbenzimidazole sulfonic acid; terephthalylidene dicamphor sulfonic acid; drometrizole trisiloxane; methyl anthranilate; rutin and derivatives thereof and orizanol and derivatives thereof.

Preferred examples of the whitening agent include: hydroquinone glucoside such as arbutin and α-arbutin, and esters thereof ascorbic acid derivatives such as ascorbic acid, ascorbic acid phosphate ester salts such as ascorbic acid phosphate sodium salt and ascorbic acid phosphate magnesium salt, ascorbic acid fatty acid esters such as ascorbic acid tetraisopalmitate ester, ascorbic acid alkyl ether such as ascorbic acid ethyl ether, ascorbic acid glucoside such as ascorbic acid-2-glucoside and fatty acid ester thereof, ascorbic acid sulfate ester, and ascorbyl tocopheryl phosphate; kojic acid; ellagic acid, tranexamic acid and derivatives thereof; ferulic acid and derivatives thereof; placenta extract; glutathione; orizanol; butyl resorcinol; and plant extracts such as oil-soluble chamomilla extract, oil-soluble licorice extract, *Seikaryu* extract, and *Saxifraga sarementosa* extract.

Preferred examples of the vitamin group and derivatives thereof include: vitamin A group such as retinol, retinol acetate, and retinol palmitate; vitamin B group such as thiamine hydrochloride salt, thiamine sulfate salt, riboflavin, riboflavin acetate, pyridoxine hydrochloride, pyridoxine dioctanoate, pyridoxine dipalmitate, flavin adenine dinucleotide, cyanocobalamin, folic acids, nicotinic acid group such as nicotinic acid amide and benzyl nicotinate, and cholines; vitamin C group such as ascorbic acid and salts such as a sodium salt thereof; vitamin D; vitamin E group such as α, β, γ, δ-tocopherol; other vitamins such as pantothenic acid and biotin; ascorbic acid derivatives such as ascorbic acid phosphate ester salts such as ascorbic acid phosphate sodium salt and ascorbic acid phosphate magnesium salt, ascorbic acid fatty acid esters such as ascorbic acid tetraisopalmitate ester, ascorbyl stearate, ascorbyl palmitate, and ascorbyl dipalmitate, ascorbic acid alkyl ether such as ascorbic acid ethyl ether, ascorbic acid glucoside such as ascorbic acid-2-glucoside and fatty acid ester thereof, and ascorbyl tocopheryl phosphate; vitamin derivatives such as tocopherol derivatives such as tocopherol nicotinate, tocopherol acetate, tocopherol linoleate, tocopherol ferulate, and tocopherol phosphate; tocotrienol; and various vitamin derivatives.

Preferred examples of the agent for hair growth, the blood circulation accelerator, and the stimulant include: plant extracts/tinctures such as *Swertia japonica* extract, capsicum tincture, *Zingiber officinale* ROSC tincture, *Zingiber officinale* ROSC extract, and cantharides tincture; capsaicin; nonylic acid vanillylamide; zingerone; ichthammol; tannic acid; borneol; cyclandelate; cinnarizine; tolazoline; acetylcholine; verapamil; cepharanthine; γ-oryzanol; vitamin E and derivatives thereof such as tocopherol nicotinate and tocopherol acetate; γ-oryzanol; nicotinic acid and derivatives thereof such as nicotinic amide, benzyl nicotinate, inositol hexanicotinate, and nicotinic alcohol; allantoin; a photosensitive element 301; a photosensitive element 401; capronium chloride; pentadecanoic acid monoglyceride; flavanonol derivatives; stigmasterol or stigmastanol and glucoside thereof; and minoxidil.

Preferred examples of the hormones include estradiol, estrone, ethinylestradiol, cortisone, hydrocortisone, and prednisone. Examples of the anti-wrinkle agent, the anti-aging agent, the tightening agent, the cold sensing agent, the warm sensing agent, the wound healing promoter, the irritation mitigator, the analgesic, and the cell activator as other medical agents include: retinols, retinoic acids, and tocopheryl retinoate; lactic acid, glycolic acid, gluconic acid, fruit acid, salicylic acid, and glucoside and ester compounds thereof; α- or β-hydroxy acids and derivatives thereof such as hydroxycapric acid, long-chain α-hydroxy fatty acids, and long-chain α-hydroxy fatty acid cholesteryl esters; γ-amino butyric acid and γ-amino-β-hydroxy butyric acid; carnitine; carnosine; creatine; ceramides and sphingosines; caffeine and xanthin, and derivatives thereof; antioxidants/active oxygen eliminating agents such as coenzyme Q10, carotene, lycopene, astaxanthin, lutein, α-lipoic acid, platinum nanocolloid, and fullerenes; catechins; flavones such as quercetin; isoflavones; gallic acid and ester saccharide derivatives thereof; polyphenols such as tannin, sesamin, protoanthocyanidin, chlorogenic acid, and apple polyphenols; rutin and derivatives thereof such as glucoside thereof; hesperidin and derivatives thereof such as glucoside thereof; lignan glucoside; substances related to licorice extract such as glabridin, glabrene, liquiritin, and isoliquiritin; lactoferrin; shogaol and gingerol; perfumery material such as menthol and cedrol, and derivatives thereof; capsaicin and vanillin, and derivatives thereof; insect repellents such as diethyltoluamide; and complexes of biologically active substances and cyclodextrins.

Examples of the plant/animal/microbe extracts include: extracts such as iris extract, *Angelica keiskei* extract, hiba arborvitae extract, asparagus extract, avocado extract, *Hydrangea serrata* extract, almond extract, althea extract, arnica extract, aloe extract, apricot extract, apricot kernel extract, *Gingko biloba* extract, *Artemisia capillaris* flower extract, fennel fruit extract, turmeric root extract, oolong tea extract, bearberry leaf extract, *Rosa multiflora* extract, *Echinacea angustifolia* leaf extract, *isodon japonicus* extract, *Scutellaria baicalensis* root extract, phellodendron bark extract, coptis rhizome extract, *Hordeum vulgare* seed extract, *panax ginseng* extract, *Hypericum erectum* extract, *Lamium album* extract, *Ononis spinosa* extract, *Nasturtium officinale* extract, orange extract, dried sea water, sea weed extract, Japanese persimmon leaf extract, *Pyracantha fortuneana* extract, hydrolyzed elastin, hydrolyzed wheat flour, hydrolyzed silk, pueraria root extract, Chamomile extract, oil-soluble Chamomile extract, carrot extract, *Artemisia capillaris* flower extract, wild oat extract, karkade extract, licorice extract, oil-soluble licorice extract, kiwi fruit extract, kiou extract, *Auricularia auricula-judae* extract, cinchona bark extract, cucumber extract, paulownia leaf extract, guanosine, guava extract, *sophora* root extract, *Gardenia florida* extract, *Sasa veitchii* extract, *Sophora angustifolia* extract, walnut extract, Japanese chestnut extract, grapefruit extract, clematis extract, black rice extract, brown sugar extracted substance, black vinegar, chlorella extract, *Moms alba* root extract, *Gentiana lutea* extract, geranium herb extract, black tea extract, yeast extract, magnolia bark extract, coffee extract, burdock extract, rice extract, fermented rice extract, fermented rice bran extract, rice germ oil, comfrey extract, collagen, *Vaccinium vitis-idaea* extract, *Asiasarum* root extract, bupleurum root extract, umbilical extract, saffron extract, *Salvia officinalis* extract, *Saponaria officinalis* extract, *Sasa* bamboo grass extract, *Crataegus cuneata* fruit extract, *Bombyx mori excrementum* extract, *Zanthoxylum piperitum* extract, shiitake extract, *Rehmannia* root extract, *Lithospermum erythrorhizone* root extract, *Perilla frutescens* extract, *Tilia cordata* flower extract, *Filipendula multijuga* extract, *Jatoba* extract, *Paeonia albiflora* extract, *Zingiber officinale* ROC extract, *Acorns calamus* root extract, *Betula alba* extract, *Tremella fusciformis* extract, *Equisetum arvense* extract, *Stevia rebaudiana* extract, *Stevia rebaudiana* fermentation product, *Seikaryu* extract, *Hedera helix* L. extract, *Crataegus oxyacantha* extract, *Sambucus nigra* extract, *Achillea millefolium* extract, *Mentha piperita* leaf extract, sage extract, *Malva sylvestris* extract, *Cnidium officinale* root extract, *Swertia japonica* extract, mulberry bark extract, rhubarb extract, soybean extract, zizyphi fructus extract, thyme extract, dandelion extract, *Lichenes* extract, tea extract, *Eugenia caryophyllus* flower extract, *Imperata cylindrica* extract, *Aurantii nobilis pericarpium* extract, tea tree oil, *Tencha* extract, red pepper extract, angelica root extract, *Calendula officinalis* extract, *Persicae semen* extract, *Citrus aurantium* peel extract, *Houttuynia cordata* extract, tomato extract, natto extract, ginseng extract, garlic extract, *Rosa canina* fruit extract, hibiscus extract, *Ophiopogon tuber* extract, *Nelumbo nucifera* extract, parsley extract, birch extract, honey, hamamelis extract, *Parietaria officinalis* extract, *Isodonis japonicus* extract, bisabolol, *Chamaecyparis obtusa* extract, *Lactobacillus bifidus* extract, *Eriobotrya japonica* extract, coltsfoot flower extract, *Petasites japonicus* extract, *Poria cocos* extract, butcher's broom extract, grape extract, grape seed extract, propolis extract, *Luffa cylindrica* fruit extract, safflower flower extract, peppermint extract, *Tilia miqueliana* extract, *Paeonia suffruticosa* root extract, hops extract, *Rosa rugosa* flower extract, pine cone extract, horse chestnut extract, Japanese skunk cabbage extract, *Sapindus mukurossi* peel extract, melissa extract, *Cladosiphon okamuranus* extract, peach extract, *Centaurea cyanus* flower extract, eucalyptus extract, *Saxifraga sarementosa* extract, *Citrus junos* extract, lily extract, coix seed extract, *Artemisia princeps* extract, lavender extract, green tea extract, eggshell membrane extract, apple extract, rooibos tea extract, lychee extract, lettuce extract, lemon extract, *Forsythiae fructus* extract, *Astragalus sinicus* extract, rose extract, rosemary extract, Roman chamomile extract, royal jelly extract, and *Sanguisorba officinalis* extract.

Examples of the antipruritic agent include diphenhydramine hydrochloride, chlorpheniramine maleate, camphor, and a substance-P inhibitor.

Examples of the corneum releasing/dissolving agent include salicylic acid, sulfur, resorcin, selenium sulfide, and pyridoxine.

Examples of the antiperspirant include chlorohydroxyaluminum, aluminum chloride, zinc oxide, and zinc p-phenolsulfonate.

Examples of the refrigerant include menthol and methyl salicylate.

Examples of the astringent agent include citric acid, tartaric acid, lactic acid, aluminum potassium sulfate, and tannic acid.

Examples of the enzyme include superoxide dismutase, catalase, lysozyme chloride, lipase, papain, pancreatin, and protease.

Preferred examples of the nucleic acids include ribonucleic acids and salts thereof, deoxyribo nucleic acids and salts thereof, and adenosine triphosphate disodium.

Preferred examples of the perfume include synthetic perfumes, natural perfumes, and various compound perfumes such as acetyl cedrene, amylcinnamaldehyde, allyamyl glycolate, β-ionone, Iso E Super, isobutyl quinoline, iris oil, irone, indole, ylang ylang oil, undecanal, undecenal, γ-undecalactone, estragole, eugenol, oakmoss, Opopanax resinoid, orange oil, eugenol, aurantiol, galaxolide, carvacrol, 1-carvone, camphor, canon, carrot seed oil, clove oil, methyl cinnamate, geraniol, geranyl nitrile, isobornyl acetate, geranyl acetate, dimethylbenzylcarbinyl acetate, styralyl acetate, cedryl acetate, terpinyl acetate, p-tert-butylcyclohexyl acetate, vetiveryl acetate, benzyl acetate, linalyl acetate, isopentyl salicylate, benzyl salicylate, sandal wood oil, santalol, cyclamen aldehyde, cyclopentadecanolide, methyl dihydrojasmonate, dihydromyrcenol, Jasmine Absolute, jasmine lactone, cis-jasmone, citral, citronellol, citronellal, cinnamon bark oil, 1,8-cineole, cinnamaldehyde, Styrax resinoid, cedar wood oil, cedrene, cedrol, celery seed oil, thyme oil, damascone, damascenone, thymol, tuberose absolute, decanal, decalactone, terpineol, γ-terpinene, triplal, nerol, nonanal, 2,6-nonadienol, nonalactone, patchouli alcohol, Vanilla Absolute, vanillin, basil oil, patchouli oil, hydroxycitronellal, α-pinene, piperitone, phenethyl alcohol, phenylacetoaldehyde, petitgrain oil, hexylcinnamaldehyde, cis-3-hexenol, Peruvian balsam, vetiver oil, vetiverol, peppermint oil, pepper oil, heliotropin, Bergamot oil, benzyl benzoate, borneol, myrrh resinoid, musk ketone, methylnonylacetoaldehyde, γ-methylionone, menthol, 1-menthol, 1-menthone, eucalyptus oil, β-ionone, lime oil, lavender oil, d-limonene, linalool, lyral, lilial, lemon oil, Rose Absolute, rose oxide, rose oil, rosemary oil, and various refined oils.

Preferred examples of the dyestuff, the colorant, the dye, and the pigment include: legal dyestuffs such as Brown No. 201, Black No. 401, Violet No. 201, Violet No. 401, Blue No. 1, Blue No. 2, Blue No. 201, Blue No. 202, Blue No. 203, Blue No. 204, Blue No. 205, Blue No. 403, Blue No. 404, Green No. 201, Green No. 202, Green No. 204, Green No. 205, Green No. 3, Green No. 401, Green No. 402, Red No. 102, Red No. 104-1, Red No. 105-1, Red No. 106, Red No. 2, Red No. 201, Red No. 202, Red No. 203, Red No. 204, Red No. 205, Red No. 206, Red No. 207, Red No. 208, Red No. 213, Red No. 214, Red No. 215, Red No. 218, Red No. 219, Red No. 220, Red No. 221, Red No. 223, Red No. 225, Red No. 226, Red No. 227, Red No. 228, Red No. 230-1, Red No. 230-2, Red No. 231, Red No. 232, Red No. 3, Red No. 401, Red No. 404, Red No. 405, Red No. 501, Red No. 502, Red No. 503, Red No. 504, Red No. 505, Red No. 506, Orange No. 201, Orange No. 203, Orange No. 204, Orange No. 205, Orange No. 206, Orange No. 207, Orange No. 401, Orange No. 402, Orange No. 403, Yellow 201, Yellow 202-1, Yellow 202-2, Yellow 203, Yellow 204, Yellow 205, Yellow 4, Yellow 401, Yellow 402, Yellow 403-1, Yellow 404, Yellow 405, Yellow 406, Yellow 407, and Yellow 5; Acid Red 14 and other acid dyes; basic dyes such as Arianor Sienna Brown, Arianor Madder Red, Arianor Steel Blue, and Arianor Straw Yellow; nitro dyes such as HC Yellow 2, HC Yellow 5, HC Red 3,4-hydroxypropylamino-3-nitrophenol, N,N'-bis(2-hydroxyethyl)-2-nitro-p-phenylenediamine, HC Blue 2, and Basic Blue 26; disperse dyes; inorganic white pigments such as titanium dioxide and zinc oxide; inorganic red-based pigments such as iron oxide (red iron oxide) and iron titanate; inorganic brown-based pigments such as γ-ferric oxide; inorganic yellow-based pigments such as yellow iron oxide and ocher; inorganic black-based pigments such as black iron oxide and black lower-order titanium oxide; inorganic violet-based pigments such as mango violet and cobalt violet; inorganic green-based pigments such as chromium oxide, chromium hydroxide, and cobalt titanate; inorganic blue-based pigments such as ultramarine and Prussian blue; pearl pigments such as titanium oxide-coated mica, titanium oxide-coated bismuth oxychloride, titanium oxide-coated talc, colored titanium oxide-coated mica, bismuth oxychloride, and fish scale guanine; metal powder pigments such as an aluminum powder, a copper powder, and gold; surface-treated inorganic and metal powder pigments; organic pigments such as a zirconium, barium, or aluminum lake; surface-treated organic pigments; natural dyestuffs and dyes such as anthraquinones such as astaxanthin and alizarin, anthocyanidine, naphthoquinones such as β-carotene, catenal, capsanthin, chalcone, carthamin, quercetin, crocin, chlorophyll, curcumin, cochineal, and shikonin, bixin, flavones, betacyanidine, henna, hemoglobin, lycopene, riboflavin, and rutin; intermediates for oxidation dyes and couplers such as p-phenylenediamine, toluene-2,5-diamine, o-, m-, or p-aminophenol, m-phenylenediamine, 5-amino-2-methylphenol, resorcin, 1-naphthol, and 2,6-diaminopyridine, and salts thereof; naturally oxidized-type dyes such as indoline; and dihydroxyacetone.

Preferred examples of the antiphlogistic agent and the antiinflammatory agent include: glycyrrhizic acid and derivatives thereof; glycyrrhetic acid derivatives; salicylic acid derivatives; hinokitiol; guaiazulene; allantoin; indomethacin; ketoprofen; ibuprofen; diclofenac; loxoprofen; Celecoxib; Infliximab; Etanercept; zinc oxide; hydrocortisone acetate; prednisone; diphenhydramine hydrochloride; chlorpheniramine maleate; and plant extracts such as peach leaf extract and *Artemisia princeps* leaf extract.

Preferred examples of the antiasthmatic agent, the antichronic obstructive pulmonary disease agent, the antiallergic agent, and the immunomodulators include aminophylline, theophyllines, steroids (fluticasone, beclomethasone, and the like), leukotriene antagonists, thromboxane inhibitors, intal, β-2 stimulants (formoterol, salmeterol, albuterol, tulobuterol, clenbuterol, epinephrine, and the like), tiotropium, ipratropium, dextromethorphan, dimemorfan, bromhexine, tranilast, ketotifen, azelastine, cetirizine, chlorpheniramine, mequitazine, tacrolimus, cyclosporine, sirolimus, methotrexate, cytokine regulating agents, interferon, omalizmab, and protein/antibody formulations.

Preferred examples of the anti-infectious disease agent and the antifungal agent include oseltamivir and zanamivir, and itraconazole. In the composition of the dispersion of the present invention, there may be blended as additives other than the above additives, publicly known ingredients for cosmetics, medicines, and foods such as ingredients described in the Japanese Standards of Cosmetic Ingredients, the Japanese Cosmetic Ingredients Codex, the Japan Cosmetic Industry Association list of displayed names of ingredients, the INCI dictionary (the International Cosmetic Ingredient Dictionary and Hand book), the Japanese Standards of Quasi-drug Ingredients, the Japanese Pharmacopoeia, the Japanese Pharmaceutical Excipients, and the Japan's Specifications and Standards for Food Additives, and ingredients described in Patent Publications and Patent Unexamined Application Publications (including Japanese or each language Translation of PCT International Application Publications and Re-publications of PCT International Publications) of Japan and various other countries, which are classified by the International Patent Classification into the classes A61K7 and A61K8, in a publicly known combination and in a publicly known blending ratio/blending amount.

<Method for Forming Hydrogel>

In the present invention, by using the above-described dispersion, that is, a dispersion containing a lipid peptide type compound, a specific alcohol, and a polymer emulsifier, and a dispersion containing further a heat resistance improver, a hydrogel can be formed by the following processes:

a) a process of adding the above dispersing agent to water and heating the resultant mixture at a temperature of room temperature or higher and lower than 100° C., and b) a process of cooling down the mixture with stirring until the temperature of the mixture becomes lower than the temperature in the heating process and forming a gel.

The above-described additive for cosmetics or additive for quasi-drugs can be added to water simultaneously together with the dispersing agent in the process a).

In the process a), the temperature for heating is preferably 50° C. to 90° C., more preferably 60° C. to 90° C., for example 80° C. Preferably, the mixture is stirred while being heated.

In the process a), although the time for heating and stirring the mixture is not particularly limited, for example, the time for heating is for 6 hours immediately after the addition of the dispersing agent, preferably can be appropriately selected from a period between 30 minutes to 3 hours after the addition of the dispersing agent.

In the process a), the amount of the added dispersion is, for example 5 to 40% by mass, preferably 5 to 20% by mass, more preferably 5 to 10% by mass, based on the total mass of the obtained hydrogel.

Subsequently to the process a), a process b) is performed in which the mixture is cooled down with stirring until the temperature of the mixture becomes lower than the temperature in the process a).

Here, the temperature to which the mixture is cooled down is room temperature to 80° C., preferably room temperature to 40° C.

<Hydrogel>

The hydrogel formed using the above dispersion and the gel obtained by the above production method are also within the scope of the present invention.

EXAMPLES

Hereinafter, the present invention is described in detail referring to Examples and Test Examples which should not be construed as limiting the present invention.

Synthesis Example 1: Synthesis of Lipid Peptide (N-Palmitoyl-Gly-His)

The lipid peptide used as the gelator in the present example was synthesized by the method described below.

Into a 500 mL four-neck flask, 14.2 g (91.6 mmol) of histidine, 30.0 g (91.6 mmol) of N-palmitoyl-Gly-methyl, and 300 g of toluene were charged and thereto, 35.3 g (183.2 mmol) of a 28% methanol solution of sodium methoxide as a base was added, followed by heating the resultant reaction mixture on an oil bath at 60° C. and continuing to stir the reaction mixture for 1 hour. The oil bath was then removed and the reaction mixture was left to be cooled down to 25° C. The reaction mixture was subjected to reprecipitation in 600 g of acetone and the resultant precipitate was filtered. The obtained solid was dissolved in a mixed solution of 600 g of water and 750 g of methanol and to the resultant solution, 30.5 mL (183.2 mmol) of a 6N hydrochloric acid was added to neutralize the solution to deposit a solid, followed by filtering the solid. Next, the obtained solid was dissolved in a mixed liquid of 120 g of tetrahydrofuran and 30 g of water at 60° C. and to the resultant solution, 150 g of ethyl acetate was added, followed by cooling down the resultant mixture from 60° C. to 30° C. A deposited solid was then filtered. Further, the obtained solid was dissolved in a solvent of 120 g of tetrahydrofuran and 60 g of acetonitrile and the resultant solution was heated to 60° C., followed by stirring the solution for 1 hour. The solution was cooled down and the resultant precipitate was filtered. The obtained solid was washed with 120 g of water and the solid was filtered, followed by drying the solid under reduced pressure to obtain 26.9 g (yield: 65%) of a white crystal of an N-palmitoyl-Gly-His free form (hereinafter, called also merely Pal-GH).

Example 1 to Example 5, Comparative Example 1 to Comparative Example 3: Preparation of Dispersion of N-Palmitoyl-Gly-his and Evaluation of Dispersibility Thereof Into a sample tube (No. 7; manufactured by Maruemu Corporation), the Pal-GH obtained by the above Synthesis Example and one of various alcohols and/or water shown in Table 1 were charged after being weighed so that the composition of the mixture became the composition (% by mass) shown in Table 1. The resultant mixture was heated and stirred at 80° C. to obtain a Pal-GH dispersion.

The dispersibility of the Pal-GH after heating and stirring the mixture at 80° C. was visually evaluated according to such a criterion that a dispersion in which the Pal-GH powder was homogeneously dispersed was evaluated as ○ and a dispersion in which the Pal-GH powder was not homogeneously dispersed (for example, one in which a block of the Pal-GH powder was observed) was evaluated as X.

The obtained results are also shown in Table 1.

TABLE 1

| | | Example | | | | | Comparative Example | | |
|---|---|---|---|---|---|---|---|---|---|
| | | 1 | 2 | 3 | 4 | 5 | 1 | 2 | 3 |
| Composition (% by mass) | Pal-GH | 20 | 20 | 10 | 20 | 10 | 10 | 10 | 10 |
| | 1,2-Pentanediole*[1] | 80 | | | | | | | |
| | 1,2-Hexanediole*[1] | | 80 | 90 | | | | | |
| | 2-Ethyl-1,3-hexanediol*[2] | | | | 60 | | | | |
| | Ethylene glycol monobutyl ether*[3] | | | | | 80 | | | |
| | Glycerin | | | | | | 90 | | |
| | Propylene glycol | | | | | | | 90 | |
| | Pure water | | | | 20 | 10 | | | 90 |
| Dispersibility of Pal-GH at 80° C. | | ○ | ○ | ○ | ○ | ○ | X | X | X |

*[1]manufactured by ITO, Inc.
*[2]manufactured by KYOWA HAKKO CHEMICAL CO., LTD. (at present: KH Neochem Co., Ltd.)
*[3]manufactured by Tokyo Chemical Industry Co., Ltd.

Examples 6 to 10, Comparative Example 4: Gelation Test by Using Pal-GH Dispersion and Propylene Glycol Alginate in Combination Into a 300 mL tall beaker, as shown in Table 2, pure water, and propylene glycol alginate (called also PG alginate) or xanthan gum were charged, and the resultant mixture was heated and stirred at 80° C. The stirring was performed using LABORATORY HIGH MIXER manufactured by AS ONE Corporation at 200 rpm.

Next, 5.0 g of each of the Pal-GH dispersions of Example 1 to Example 5 that were heated to 80° C. was added thereto and the resultant mixture was further heated and stirred for 5 minutes.

After the stop of the heating, the mixture was stirred and cooled down until the temperature of the mixture reached around 40° C. and it was confirmed whether a gel was formed. The confirmation of the formation of the gel was performed by the test tube inversion method and a state in which the fluidity of the dispersion was lost and when the tall beaker was inverted, the dispersion did not flow down was evaluated as "gelled (○)". On the contrary, a state in which no gel formation was observed was evaluated as "x". The final composition after the gelation test and the obtained test results are shown in Table 2.

TABLE 2

| Composition (% by mass) | | Example | | | | | Comparative Example |
|---|---|---|---|---|---|---|---|
| | | 6 | 7 | 8 | 9 | 10 | 4 |
| Dispersion | Dispersion of Example 1 | 5.0 | | | | | 5.0 |
| | Dispersion of Example 2 | | 5.0 | | | | |
| | Dispersion of Example 3 | | | 5.0 | | | |
| | Dispersion of Example 4 | | | | 2.5 | | |
| | Dispersion of Example 5 | | | | | 5.0 | |
| PG alginate*[1] | | 0.3 | | | | | |
| PG alginate*[2] | | | 0.2 | 0.2 | 0.3 | 0.2 | |
| Xanthan gum | | | | | | | 0.3 |
| Pure water | | 94.7 | 94.8 | 94.7 | 97.2 | 94.7 | 94.7 |
| Gelation | | ○ | ○ | ○ | ○ | ○ | X |

*[1]manufactured by Junsei Chemical Co., Ltd.; reagent for chemical use
*[2]manufactured by KIMICA Corporation; KIMILOID HV (viscosity of 1% solution at 20° C.: 150 to 250 mPa · s)

Example 11 and Example 12: Preparation of Premix

To the dispersion of Example 3 or Example 5, 0.3 g in total of PG alginate was added and thereto, further 14.7 g of pure water was added to prepare a premix.

TABLE 3

| Composition (% by mass) | | Example 11 | Example 12 |
|---|---|---|---|
| Dispersion | Dispersion of Example 3 | 25.0 | |
| | Dispersion of Example 5 | | 25.0 |
| | PG alginate*[1] | 1.0 | 1.0 |
| | PG alginate*[2] | 0.5 | 0.5 |
| | Water | 73.5 | 73.5 |

*[1]manufactured by KIMICA Corporation; KIMILOID HV (viscosity of 1% solution at 20° C.: 150 to 250 mPa · s)
*[2]manufactured by Kikkoman Biochemifa Company; Duck Loid PF (viscosity of 1% solution at 20° C.: 45 to 55 mPa · s)

Example 13 and Example 14: Gelation Test by Using Premix

Into a 300 mL tall beaker, 80 g of pure water was charged and was heated and stirred at 80° C. The stirring was performed using LABORATORY HIGH MIXER manufactured by AS ONE Corporation at 200 rpm.

Next, to pure water, 20 g of the premix of Example 11 or Example 12 that was heated to 80° C. was added and the resultant mixture was further heated and stirred for 5 minutes (at 80° C. and at 200 rpm).

After the stop of the heating and the stirring, the mixture was stirred and cooled down until the temperature of the mixture reached around 40° C. and it was confirmed whether a gel was formed. The confirmation of the formation of the gel was performed by the above-described test tube inversion method and it was evaluated whether a gel was formed. The obtained test results are shown in Table 4.

TABLE 4

| Composition (% by mass) | | Example 13 | Example 14 |
|---|---|---|---|
| Premix | Example 11 | 20.0 | |
| | Example 12 | | 20.0 |
| Pure water | | 80.0 | 80.0 |
| Gelation | | ○ | ○ |

Example 15 to Example 18: Evaluation of Gelation and Thermal Stability of Fatty Acid-Containing Gel Using Premix Into a 300 mL tall beaker, pure water was charged and was heated and stirred at 80° C. The stirring was performed using LABORATORY HIGH MIXER manufactured by AS ONE Corporation at 200 rpm.

Separately, to 20 g of the premix of Example 11 that was heated to 80° C., a fatty acid (lauric acid, palmitic acid, or stearic acid) was added to heat and dissolve the fatty acid in the premix. The fatty acid-containing premix was added to pure water that was previously heated and stirred at 80° C. and the resultant mixture was further heated and stirred for 5 minutes (at 80° C. and at 200 rpm).

After the stop of the heating, the mixture was stirred and cooled down until the temperature of the mixture reached around 40° C. and it was confirmed whether a gel was formed. The confirmation of the formation of the gel was performed by the above-described test tube inversion method and it was evaluated whether a gel was formed. The obtained test results and the final composition after the gelation test are shown in Table 5.

The prepared gel was preserved in a thermostat of 40° C. over one night and the thermal stability of the gel was evaluated. After the preservation of the gel, a gel in which a deposit or syneresis was hardly observed was evaluated as "○" and a gel in which a large amount of deposits or syneresis was observed was evaluated as "x". The obtained results are also shown in Table 5.

TABLE 5

| Composition (% by mass) | Example 15 | Example 16 | Example 17 | Example 18 |
|---|---|---|---|---|
| Premix of Example 11 | 20.0 | 20.0 | 20.0 | 20.0 |
| Lauric acid | | 0.04 | | |
| Palmitic acid | | | 0.05 | |
| Stearic acid | | | | 0.06 |
| Pure water | 80.0 | 79.86 | 79.95 | 79.94 |
| Gelation | ○ | ○ | ○ | ○ |
| Thermal stability after preservation at 40° C. | X | ○ | ○ | ○ |

Example 19: Gelation Test by Using Premix

Into a 300 mL tall beaker, 90 g of pure water was charged and was heated and stirred at 80° C. The stirring was performed using LABORATORY HIGH MIXER manufactured by AS ONE Corporation at 200 rpm.

Next, to pure water, 10 g of a premix having a composition below that was heated to 80° C. was added and the resultant mixture was further heated and stirred for 5 minutes (at 80° C. and at 200 rpm).

After the stop of the heating and the stirring, the mixture was stirred and cooled down until the temperature of the mixture reached around 40° C. and it was confirmed whether a gel was formed. The confirmation of the formation of the gel was performed by the above-described test tube inversion method and it was evaluated whether a gel was formed.

TABLE 6

| Premix composition (% by mass) | Example 19 |
|---|---|
| Pal-GH | 7.5 |
| 1,2-hexanediol | 20.0 |
| PG alginate*[1] | 2.0 |
| PG alginate*[2] | 1.0 |
| Stearic acid | 0.6 |
| Pure water | 68.9 |

*[1]manufactured by KIMICA Corporation; KIMILOID HV (viscosity of 1% solution at 20° C.: 150 to 250 mPa · s)
*[2]manufactured by Kikkoman Biochemifa Company; Duck Loid PF (viscosity of 1% solution at 20° C.: 45 to 55 mPa · s)

The invention claimed is:

1. A method for producing a hydrogel, the method comprising:
   adding a dispersion to water and heating the resultant mixture to a temperature that is room temperature or higher and lower than 100° C.; and
   cooling down the mixture with stirring until the temperature of the mixture reaches a temperature lower than the temperature in the heating and forming a gel while the mixture is being stirred and cooled down,
   wherein the dispersion comprises:
   a polymer emulsifier;
   a lipid peptide type compound in which a peptide portion having an amino acid repeating bonding structure is bonded to a lipid portion having a $C_{9-23}$ aliphatic group wherein a blending amount of the lipid peptide type compound is 0.1% to 40% by mass based on the total mass of the dispersion; and
   (i) at least one alcohol selected from the group consisting of 1,2-alkanediol, 1,3-alkanediol, and ethylene glycol monoalkyl ether or (ii) a mixed solution of water and the at least one alcohol.

2. The method of claim 1, wherein a blending amount of the at least one alcohol is 50% to 90% by mass based on the total mass of the dispersion.

3. The method of claim 1, wherein a blending amount of the polymer emulsifier is 1.0% to 20.0% by mass based on the total mass of the dispersion.

4. The method of claim 1, wherein the blending amount of the lipid peptide type compound is 0.1% to 30% by mass based on the total mass of the dispersion.

5. The method of claim 1, wherein the temperature to which the mixture is cooled down during stirring is a temperature in the range of from room temperature to 80° C.

6. The method of claim 5, wherein the temperature to which the mixture is cooled down during stirring is 40° C.

7. The method of claim 1, wherein the at least one alcohol is selected from the group consisting of 1,2-pentanediol, 1,2-hexanediol, 1,2-octanediol, 2-ethyl-1,3-hexanediol, and ethylene glycol monoalkyl ether.

8. The method of claim 1, wherein the polymer emulsifier is at least one polymer compound selected from the group consisting of a graft polymer compound in which a hydrophobic moiety is grafted to a hydrophilic backbone and a block polymer compound containing a hydrophobic structural unit and a hydrophilic structural unit.

9. The method of claim 1, wherein the polymer emulsifier is at least one polymer compound selected from the group consisting of a carboxymethyl cellulose and an alginic acid ester.

10. The method of claim 1, wherein the polymer emulsifier is propylene glycol alginate.

11. The method of claim 1, wherein the lipid peptide type compound contains at least one member selected from the group consisting of compounds of Formula (1) to Formula (3) and pharmaceutically acceptable salts of the compounds:

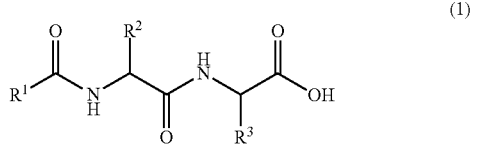

(1)

where
R$^1$ is a C$_{9-23}$ aliphatic group;
R$^2$ is a hydrogen atom or a C$_{1-4}$ alkyl group optionally having a C$_{1-2}$ branching chain;
R$^3$ is a —(CH$_2$)$_n$—X group; n is a number of 1 to 4; and
X is an amino group, a guanidino group, a —CONH$_2$ group, or a 5-membered ring optionally having 1 to 3 nitrogen atom(s), a 6-membered ring optionally having 1 to 3 nitrogen atom(s), or a fused heterocyclic ring composed of a 5-membered ring and a 6-membered ring which optionally have 1 to 3 nitrogen atom(s),

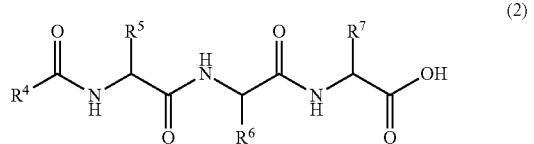

(2)

where
R$^4$ is a C$_{9-23}$ aliphatic group;
R$^5$ to R$^7$ are each independently a hydrogen atom, a C$_{1-4}$ alkyl group optionally having a C$_{1-2}$ branching chain, or a —(CH$_2$)$_n$—X group; n is a number of 1 to 4; and X is an amino group, a guanidino group, a —CONH$_2$ group, or a 5-membered ring optionally having 1 to 3 nitrogen atom(s), a 6-membered ring optionally having 1 to 3 nitrogen atom(s), or a fused heterocyclic ring composed of a 5-membered ring and a 6-membered ring which optionally have 1 to 3 nitrogen atom(s), and

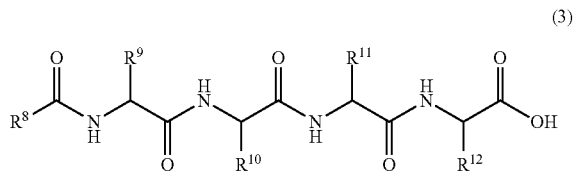

(3)

where
R$^8$ is a C$_{9-23}$ aliphatic group;
R$^9$ to R$^{12}$ are each independently a hydrogen atom, a C$_{1-4}$ alkyl group optionally having a C$_{1-2}$ branching chain, or a —(CH$_2$)$_n$—X group; n is a number of 1 to 4; and
X is an amino group, a guanidino group, a —CONH$_2$ group, or a 5-membered ring optionally having 1 to 3 nitrogen atom(s), a 6-membered ring optionally having 1 to 3 nitrogen atom(s), or a fused heterocyclic ring composed of a 5-membered ring and a 6-membered ring which optionally have 1 to 3 nitrogen atom(s).

12. The method of claim 1, wherein, prior to the heating of the resultant mixture to a temperature that is room temperature or higher and lower than 100° C., the dispersion is blended with a solvent and an additive to form a premix composition, where the additive is selected from the group consisting of a cosmetic additive and a quasi-drug additive.

13. The method of claim 1, wherein the dispersion further comprises a heat resistance improver.

14. The method of claim 13, wherein a blending amount of the heat resistance improver is 0.5% to 2.0% by mass based on the total mass of the dispersion.

15. The method of claim 13, wherein the heat resistance improver is at least one fatty acid selected from the group consisting of a saturated C$_{10-20}$ fatty acid, an unsaturated C$_{10-20}$ fatty acid, and a salt of these fatty acids.

16. The method of claim 15, wherein the heat resistance improver is capric acid, lauric acid, myristic acid, palmitic acid, or stearic acid.

17. The method of claim 1, wherein the lipid peptide type compound is homogeneously dispersed in the dispersion.

* * * * *